(12) United States Patent
Komatsu et al.

(10) Patent No.: US 7,122,713 B2
(45) Date of Patent: Oct. 17, 2006

(54) ABSORBENT ARTICLE WITH FLEXIBLE HINGE

(75) Inventors: Shimpei Komatsu, Kagawa (JP); Satoshi Mizutani, Kagawa (JP); Tatsuya Tamura, Kagawa (JP); Makoto Suekane, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 10/964,541

(22) Filed: Oct. 13, 2004

(65) Prior Publication Data
US 2005/0085783 A1 Apr. 21, 2005

Related U.S. Application Data

(63) Continuation of application No. PCT/JP03/11407, filed on Sep. 8, 2003.

(30) Foreign Application Priority Data

Sep. 9, 2002 (JP) .............................. 2002-263454
Sep. 20, 2002 (JP) .............................. 2002-276387

(51) Int. Cl.
*A61F 13/15* (2006.01)
(52) U.S. Cl. ...................... 604/380; 604/379; 604/378; 604/385.01
(58) Field of Classification Search ................ 604/378, 604/380, 385.01, 379–383
See application file for complete search history.

(56) References Cited

U.S. PATENT DOCUMENTS

| 4,059,114 | A | | 11/1977 | Richards | |
|---|---|---|---|---|---|
| 5,981,824 | A | * | 11/1999 | Luceri | ......................... 604/365 |
| 6,326,525 | B1 | * | 12/2001 | Hamajima et al. | ........... 604/378 |
| 6,695,827 | B1 | * | 2/2004 | Chen et al. | ............. 604/385.01 |
| 6,867,345 | B1 | * | 3/2005 | Shimoe et al. | ............... 604/378 |
| 2004/0243082 | A1 | * | 12/2004 | Kinoshita et al. | ........... 604/380 |
| 2005/0124951 | A1 | * | 6/2005 | Kudo et al. | .................. 604/380 |
| 2005/0148971 | A1 | * | 7/2005 | Kuroda et al. | ............... 604/380 |
| 2005/0148972 | A1 | * | 7/2005 | Miyama et al. | .............. 604/380 |
| 2005/0148973 | A1 | * | 7/2005 | Tamura et al. | ............... 604/380 |

FOREIGN PATENT DOCUMENTS

| JP | 52-138398 A1 | 11/1977 |
|---|---|---|
| JP | 5-39691 | 10/1993 |
| JP | 08-322875 A1 | 12/1996 |
| JP | 10-272156 A1 | 10/1998 |
| JP | 10-328232 | 12/1998 |
| JP | 11-033054 A1 | 2/1999 |
| JP | 11-113955 | 4/1999 |
| JP | 2002-065741 | 3/2002 |
| JP | 2002-095697 A1 | 4/2002 |

\* cited by examiner

*Primary Examiner*—Jacqueline F. Stephens
(74) *Attorney, Agent, or Firm*—Darby & Darby

(57) ABSTRACT

Disclosed is an absorbent article including: a liquid-permeable topsheet on a skin surface; and a backsheet on a garment surface. First flexible hinges and second flexible hinges are formed to extend longitudinally of the absorbent article. The first flexible hinges are disposed symmetrically about a longitudinal centerline of the absorbent article to define a central absorbent portion having an absorbent layer therebetween. The second flexible hinges are disposed symmetrically about the longitudinal centerline and spaced outwardly apart from the first flexible hinges to define support portions between adjacent first and second flexible hinges and side portions outside the second flexible hinges. The first flexible hinges facilitate bending of the support portions from the central absorbent portion, and the second flexible hinges facilitate bending of the side portions from the support portions.

25 Claims, 15 Drawing Sheets

ABSORBENT ARTICLE WITH FLEXIBLE HINGE

BACKGROUND OF THE INVENTION

1. Field of the Invention

The present invention relates to an absorbent article suitable for absorbing menstrual blood and so on discharged from the female genital organ, more particularly, relates to an absorbent article having flexible hinges that can be deformed to bring a central portion having an absorbent layer into close contact with the wearer's excretory part.

2. Related Art

Absorbent articles intended to absorb menstrual blood discharged from a female genital organ are typically constructed to include an absorbent layer, a liquid-permeable topsheet covering the skin surface of the absorbent layer, and a liquid-impermeable backsheet covering the garment surface of the absorbent layer. Generally, they are worn with the backsheet adhered to an inner side of a groin piece of an undergarment through a pressure-sensitive adhesive layer.

In order to certainly collect liquid discharged from an excretory part of a wearer by the absorbent article, the skin surface is preferably brought into close contact with the wearer's excretory part. If a clearance is caused between the skin surface of the absorbent article and the excretory part when the absorbent article is worn in the crotch, discharged liquid applied to the topsheet may flow along the topsheet to easily cause leakage laterally of the absorbent article or leakage toward the wearer's buttocks, which results in fouling the undergarment or other garments.

Particularly when the absorbent article is fixed to a groin piece of an undergarment and worn in the wearer's crotch, motion of the wearer's body easily causes displacement of the undergarment with respect to the wearer's crotch. Furthermore, when the absorbent article held between the thighs together with the groin piece of the undergarment is laterally compressed, the absorbent layer is easily laterally deformed by compression, so that a clearance is easily caused between the skin surface of the absorbent article and the wearer's excretory part, as set forth above.

Accordingly, there has been developed a technology aiming at bringing the central portion of the absorbent article into close contact with the wearer's excretory part, as disclosed in the following Patent Publications 1 and 2.

Patent Publication 1 discloses an absorbent article, in which a raised portion where an absorbent body is of an increased thickness is provided centrally while a pair of curved top-side grooves is formed on right and left sides of the raised portion. The top-side grooves can serve as flexible hinges to facilitate folding of the absorbent body, which aims at deforming the raised portion to have an arc cross-section projecting toward the wearer.

Patent Publication 2 discloses a sanitary napkin, in which an upper surface is provided, at both sides thereof, with compressed grooves extending longitudinally to approach each other at a central portion, and a lower surface is provided, at a width direction center thereof, with a compressed groove extending longitudinally to the vicinity of a rear end. When the wearer's thighs exert a stress on it, therefore, the portion extending along the compressed groove formed in the lower surface is lifted up so that the sanitary napkin can be deformed to have a W-shaped cross section, coming into suitable contact with a female private part.

[Patent Publication 1]
Japanese Unexamined Patent Publication No. 10-328232

[Patent Publication 2]
Japanese Examined Utility-Model Publication No. 5-39691

When the absorbent article disclosed in Patent Publication 1 is subjected to a compressive force, however, since the absorbent body is so bent that its skin surface forms valleys at the top-side grooves which are disposed one on each side, the raised portion between the top-side grooves tends to deform away from the wearer's skin, thereby reducing the degree of close fitting between the raised portion and the wearer's excretory part.

In addition, since the absorbent body provided in the raised portion is generally of a low density and soft so that a soft feel can be given to the wearer's crotch, the absorbent article subjected to a lateral pressure tends to cause a mere lateral compression of the raised portion rather than bending of the absorbent body at the top-side grooves. Furthermore, since the resiliency of the absorbent body decreases when discharged liquid is given to the absorbent article in such a deformed state, the absorbent body cannot be so restored as to spread from the laterally compressed state. Therefore, the area of the skin surface of the absorbent article is substantially decreased, so that discharged liquid cannot be sufficiently collected by the absorbent article.

In the sanitary napkin disclosed in Patent Publication 2, on the other hand, providing the compressed groove centrally of the back surface aims at deforming the absorbent layer to project toward the wearer's skin. However, since a soft, low-density material is used for the absorbent layer, as set forth above, its strength decreases after absorption of discharged liquid, so that the absorbent layer is easily crushed from the projecting state. As a result, it becomes difficult to keep the absorbent layer in suitable contact with the wearer's excretory part. If a high-density material is used for the absorbent layer so as to maintain the projecting state even after absorption of discharged liquid, on the other hand, a stiff feel will be given disadvantageously to the wearer's crotch.

In addition, the density of the absorbent layer is increased to have a high stiffness at the portion extending along the compressed groove formed in the back side of the sanitary napkin. Since the compressed groove is located at the mountain top when the absorbent layer is deformed in the projecting state, the portion of the compressed groove also tends to give a stiff feel to the wearer's body.

It should also be noted that the absorbent article disclosed in Patent Publication 1 is elongated and the raised portion rising from the skin surface is also elongated. However, the top-side grooves that can function as the flexible hinges are provided only on both sides of the front portion of the raised portion, without providing means for bringing the rear portion of the raised portion into close contact with the wearer's body. Therefore, it is difficult to bring the rear portion of the raised portion into dose contact with the area from the crotch to the buttocks, particularly, the perineum of a female (i.e., the area between the posterior part of the vaginal opening and the anus).

Accordingly, menstrual blood discharged from the vaginal opening is liable to leak toward the buttocks during both nighttime and daytime.

SUMMARY OF THE INVENTION

The present invention has been worked out in view of the shortcomings in the prior art set forth above and has an object to provide an absorbent article, in which a central portion having an absorbent layer can easily come into close contact with the excretory part of a wearer and such close contact can be easily maintained even after absorption of discharged liquid.

Another object of the present invention is to provide an absorbent article, in which a rear portion can easily come into close contact with the crotch of a wearer.

According to a first aspect of the present invention, there is provided an absorbent article comprising:

a liquid-permeable topsheet on a skin surface; and
a backsheet on a garment surface, wherein
first flexible hinges and second flexible hinges are formed to extend longitudinally of the absorbent article, the first flexible hinges being disposed symmetrically about a longitudinal centerline of the absorbent article to define a central absorbent portion having an absorbent layer therebetween, the second flexible hinges being disposed symmetrically about the longitudinal centerline and spaced outwardly apart from the first flexible hinges to define support portions between adjacent first and second flexible hinges and side portions outside the second flexible hinges, the first flexible hinges facilitating bending of the support portions from the central absorbent portion, and the second flexible hinges facilitating bending of the side portions from the support portions.

In the absorbent article according to the first aspect of the present invention, since the flexible hinges are provided two on either side of the centerline, the absorbent article subjected to a lateral compressive force can be bent at the individual first and second flexible hinges on either side, so that the central absorbent portion can be easily lifted up.

More specifically, when a compressive force toward the longitudinal centerline is exerted on the individual second flexible hinges, the individual support portions can be displaced to have the first flexible hinge higher than the second flexible hinge, thereby lifting up the central absorbent portion.

The support portions are stiff enough to operate as set forth above. In order to easily achieve such deformation, the individual support portions may have a layer whose density is higher than that of the absorbent layer of the central absorbent portion.

Preferably, when no external force is exerted on the absorbent article, the first and second flexible hinges are located below the midpoint of thickness of the central absorbent portion, whereas when a compressive force toward the longitudinal centerline is exerted on the individual second flexible hinges, the central absorbent portion and the support portions are deformed so that the individual first flexible hinges get under the absorbent layer provided in the central absorbent portion.

If the first and second flexible hinges are located below the midpoint of thickness of the central absorbent portion, the absorbent article can be easily deformed to lift up the central absorbent portion, as set forth above.

Preferably, the support portions approach each other the nearest at a lateral reference line of the absorbent article, and gradually go away from the centerline as they extend away from the lateral reference line toward longitudinally opposed ends of the absorbent article. For example, the individual support portions may be in the shape of a line curved toward the centerline.

With this construction, since the first and second flexible hinges can match curved surfaces of the thighs, a compressive force applied from the thighs can uniformly acts on every part of the flexible hinges.

Preferably, the individual support portions have a portion of constant width, over which the first and second flexible hinges are spaced a constant distance apart from each other.

With this construction, the central absorbent portion can be lifted up toward the wearer's skin in a well-balanced manner within a range of a predetermined length.

In an alternative, the first and second flexible hinges may extend in the shape of a straight line.

The absorbent layer may extend over the central absorbent portion, across the support portions, to the side portions.

If so, the support portions and the side portions also have liquid absorbency, so that even when discharged liquid flows laterally out of the central absorbent portion, the discharged liquid can be absorbed by the support portions and so on.

In this case, the first and second flexible hinges may be formed by compressing the absorbent layer.

It is also possible that absorbent layers provided in the support portions are separated from the absorbent layer provided in the central absorbent portion by the first flexible hinges, and absorbent layers provided in the side portions are separated from the absorbent layers provided in the support portions by the second flexible hinges.

In this case, it is preferred that the topsheet and the backsheet are bonded together at the first and second flexible hinges where no absorbent layer is present.

Preferably, the absorbent layer provided in the central absorbent portion has a higher basis weight than the absorbent layers provided in the support portions.

In this case, since the central absorbent portion is bulky, the first and second flexible hinges can be located much below the midpoint of thickness of the central absorbent portion, so that the central absorbent portion can be easily supported by the support portions after lifted up toward the wearer's skin.

The individual support portions may have a width of 5 to 15 mm, in which the absorbent layer is compressed, so that a boundary line between the support portion and the central absorbent portion functions as the first flexible hinge while a boundary line between the support portion and the side portion functions as the second flexible hinge.

It is also possible that the central absorbent portion is surrounded by the first flexible hinges and longitudinally opposed lateral flexible hinges that are connected between the first flexible hinges, and the second flexible hinges are located outside the central absorbent portion.

If the central absorbent portion is surrounded by the first flexible hinges and the lateral flexible hinges, discharged liquid can be easily prevented from diffusing beyond the central absorbent portion to a surrounding area. In addition, since the absorbent article can be easily bent at the individual flexible hinges, the absorbent article can easily deform to conform to the shape of the wearer's crotch.

In an alternative, the first flexible hinges may be located inside a region surrounded by the second flexible hinges and longitudinally opposed lateral flexible hinges that are connected between the second flexible hinges.

In this case, since the support portions defined between adjacent first and second flexible hinges are located inside the surround region, discharged liquid applied to the support portions can be easily prevented from diffusing to a surrounding area.

In the absorbent article according to the first aspect of the present invention, it is also possible that first rear flexible hinges are extended rearwardly continuously from the first flexible hinges to gradually approach each other, and second rear flexible hinges are extended rearwardly to gradually approach each other while being spaced outwardly apart from the first rear flexible hinges, to thereby define rear support portions between adjacent first and second rear flexible hinges.

In this construction, since a lifting force also acts on the rear portion of the absorbent article during wear of the undergarment in the wearer's crotch, the rear support portions can also be displaced to have the first rear flexible hinge higher than the second rear flexible hinge, so that the portion between the first rear flexible hinges can be lifted up toward the wearer's skin and supported by the rear support portions that get under it. Therefore, the portion between the first rear flexible hinges can easily come into close contact with the wearer's crotch, particularly the perineum, preventing rearward leakage of discharged liquid.

In this case, the second rear flexible hinges may be extended continuously from the second flexible hinges. In an alternative, the second rear flexible hinges may be separated from the second flexible hinges.

Also in this case, the first and second rear flexible hinges may be formed by compressing the absorbent layer.

Here, a rear central absorbent portion may be defined between the first rear flexible hinges, and the rear support portions may have an absorbent layer that is of a higher density than that provided in the rear central absorbent portion.

With the high-density absorbent layer provided in the rear support portions, the rear central absorbent portion can be easily lifted up toward the wearer's crotch.

According to a second aspect of the present invention, there is provided an absorbent article comprising:

a liquid-permeable topsheet on a skin surface; and a backsheet on a garment surface, wherein first rear compressed portions are disposed symmetrically about a longitudinal centerline of the absorbent article to define a rear central absorbent portion having an absorbent layer therebetween, the first rear compressed portions extending rearwardly of the absorbent article to gradually approach each other, and second rear compressed portions are disposed symmetrically about the longitudinal centerline, the second rear compressed portions extending rearwardly of the absorbent article while being spaced outwardly apart from the first rear compressed portions, wherein front ends of the second rear compressed portions are located closer to a rear end edge of the absorbent article than portions between which the first rear compressed portions have a maximum lateral separation distance, and the front ends face the first rear compressed portions at a predetermined spacing.

When the absorbent article according to the second aspect of the present invention is worn in the wearer's crotch and subjected to a tightening force from the undergarment, this force is exerted on the second rear compressed portions, so that the front ends of the second rear compressed portions are displaced to get under the first rear compressed portions, thereby functioning to lift up the rear central absorbent portion. Therefore, the rear central absorbent portion can easily come into close contact with the wearer's crotch. Particularly because the wide portion of the rear central absorbent portion where the first rear compressed portions have a maximum lateral separation distance can be lifted up by the front ends of the second rear compressed portions, the wide portion can easily come into contact with the perineum, preventing rearward leakage of discharged liquid.

Preferably, portions defined between adjacent first and second rear compressed portions have an absorbent layer that is of a higher density than that provided in the rear central absorbent portion. In this case, because high-density, stiff rear support portions can be formed between the adjacent first and second rear compressed portions, the rear central absorbent portion can be easily lifted up toward the perineum.

In one embodiment, an imaginary extension, which is extended forwardly from the front end of the second rear compressed portion in parallel with the longitudinal centerline, may intersect the first rear compressed portion.

With this construction, when a longitudinal force is exerted on the second rear compressed portion, the front end of the second rear compressed portion can be easily displaced to get under the first rear compressed portion, so that the wide portion of the rear central absorbent portion can be easily lifted up toward the perineum.

In another embodiment, additional compressed portions may be formed at the front ends of the second rear compressed portions and placed side by side with the first rear compressed portions.

With this construction, the rear central absorbent portion can be easily lifted up due to the rear support portions formed between the first rear compressed portions and the additional compressed portions.

In yet another embodiment, first compressed portions may be extended forwardly from the first rear compressed portions to gradually approach each other until a lateral reference line of the absorbent article.

With this construction, since a central absorbent portion extending continuously forwardly from the front, wide portion of the rear central absorbent portion is gradually narrowed, the wide portion of the rear central absorbent portion can be locally deformed by the front ends of the second rear compressed portions to come into contact with the perineum.

Preferably, a longitudinal shrinkage force is exerted on the absorbent article, at least at locations where the front ends of the second rear compressed portions face the first rear compressed portions.

With the shrinkage force, the absorbent article can be easily deformed so that the front ends of the second rear compressed portions get under the first rear compressed portions.

The absorbent articles according to the present invention are particularly suitable for use as a sanitary napkin.

In case of sanitary napkin, the skin surface of the absorbent article need be deformed to project centrally toward the wearer's vaginal opening so as to come into close contact with the vaginal opening. In the present invention, since the central absorbent portion can be always lifted up toward the vaginal opening, the central absorbent portion can be easily kept in close contact with the vaginal opening as well as the perineum.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

In the present invention, the absorbent article refers to devices which are intended to be worn in the crotch of a wearer to absorb various exudates discharged from the wearer's body, such as menstrual blood, urine, and vaginal discharge, but in the following embodiments, the absorbent article is shown embodied in a sanitary napkin whose primary object is to absorb menstrual blood discharged from the vaginal opening of a woman. It should be noted that the absorbent article has two major surfaces: of which one surface intended to be worn toward the wearer's crotch is referred to as "skin surface", while the other surface is referred to as "garment surface" regardless of whether a garment is worn outside the absorbent article or not.

As used herein, the term "flexible hinge" refers to a boundary line between two regions, wherein the boundary line has a different stiffness from the two regions, facilitating bending of one region from the other region. The flexible hinge may extend either continuously or intermittently in the longitudinal direction of the absorbent article.

As used herein, the term "longitudinal centerline" refers to a line which extends longitudinally to divide the absorbent article laterally in two. On the other hand, the term "lateral reference line" does not necessarily refer to a line which extends laterally to divide the absorbent article longitudinally in two. In the following embodiments where right and left first compressed portions are not parallel with each other, a line which extends laterally at a location where the right and left first compressed portions approach each other the nearest, is taken as the lateral reference line. If the location where the right and left first compressed portions approach each other the nearest cannot be specified, such as when they are parallel with each other, a line which extends laterally to cross a longitudinal center of a portion intended to be brought into contact with the vaginal opening during wear, is taken as the lateral reference line.

Figure 1:
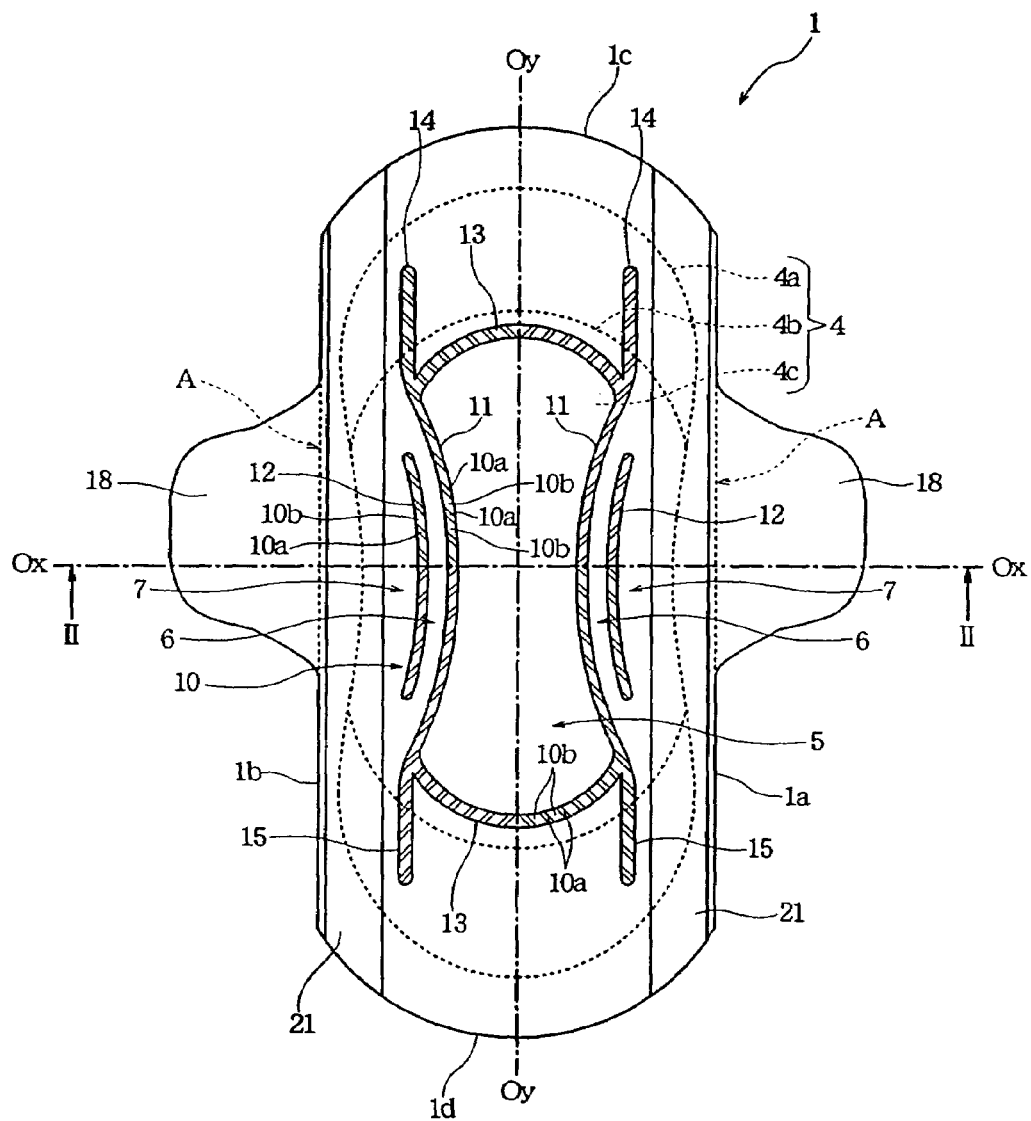
FIG. 1 is a top plan view showing a sanitary napkin as an absorbent article according to a first embodiment of the present invention.
Figure 2:
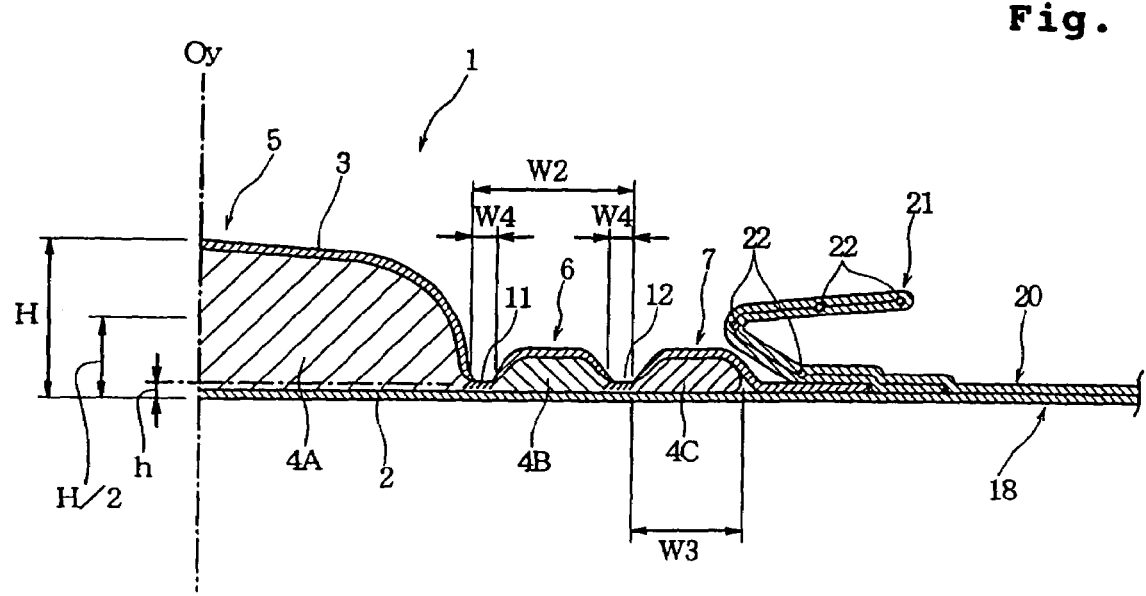
FIG. 2 is a half sectional view of the sanitary napkin taken along line II—II of FIG. 1.
Figure 3:
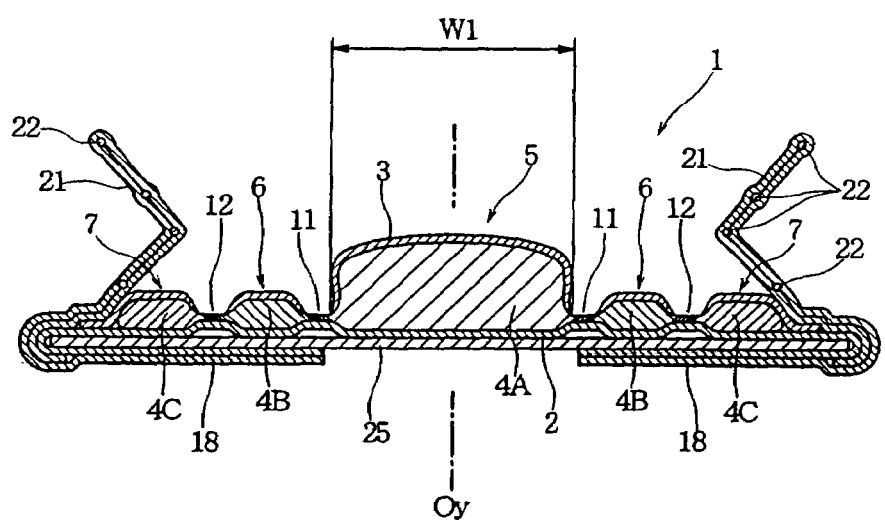
FIG. 3 is a sectional view showing a state where the sanitary napkin of FIG. 1 is attached to a groin piece of an undergarment.
Figure 4:
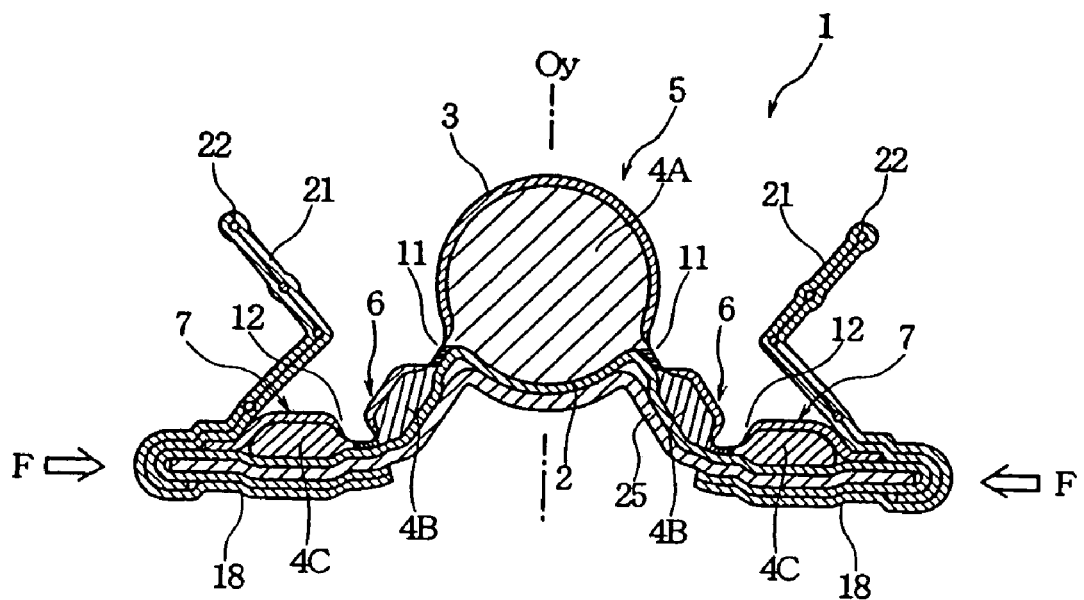
FIG. 4 is a sectional view showing a state where the groin piece and the sanitary napkin are deformed due to a lateral compressive force.
Figure 5:
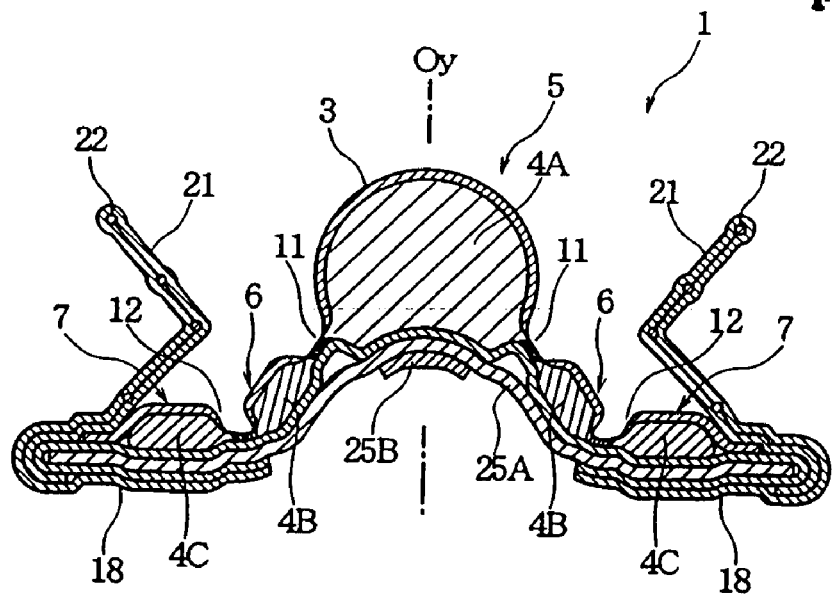
FIG. 5 is a sectional view showing a deformed state where the sanitary napkin is attached to a groin piece of a tight undergarment.

FIG. 1 is a top plan view showing a sanitary napkin 1 as an absorbent article according to a first embodiment of the present invention, wherein the skin surface faces upward; FIG. 2 is a half sectional view of the sanitary napkin taken along line II—II of FIG. 1; FIG. 3 is a sectional view showing a state where the sanitary napkin is attached to a groin piece of an undergarment; FIG. 4 is a sectional view showing a state where the groin piece and the sanitary napkin are deformed due to a lateral compressive force; and FIG. 5 is a sectional view showing a state where the sanitary napkin is attached to a groin piece of another undergarment which can exert a larger tightening force on the wearer's crotch.

As shown in the top plan view of FIG. 1, the sanitary napkin 1 is of an elongated shape, wherein longitudinally extending right and left side edges 1a and 1b are laterally spaced a constant distance apart from a longitudinal centerline Oy—Oy, while front and rear end edges 1c and 1d in the shape of an outwardly curved line are longitudinally spaced apart from a lateral reference line Ox—Ox. It should be noted that in the case where the sanitary napkin is provided with wings 18 and 18, as shown in FIG. 1, the right and left side edges 1a and 1b will be described as inclusive of imaginary cut lines A and A extending along bases of the wings 18 and 18.

As shown in the sectional views of FIGS. 2 through 5, the sanitary napkin 1 has a liquid-impermeable backsheet 2 appearing on the garment surface and a liquid-permeable topsheet 3 appearing on the skin surface. Between the backsheet 2 and the topsheet 3, disposed is an absorbent layer 4. The absorbent layer 4 is constructed to include: a first absorbent layer 4a whose periphery is shown by a dotted line in FIG. 1; a second absorbent layer 4b having a smaller area than the first absorbent layer 4a and laid on the first absorbent layer 4a, whose periphery is also shown by a dotted line in FIG. 1; and a third absorbent layer 4c having a smaller area than the second absorbent layer 4b and laid on the second absorbent layer 4b within a central absorbent portion 5 of an hourglass shape.

Here, at least the topsheet 3 and the absorbent layer 4 are compressed to form compressed portions 10. The compressed portions 10 are formed by embossing with a heating roller, wherein the first absorbent layer 4a, the second absorbent layer 4b, the third absorbent layer 4c and the topsheet 3 are stacked one upon another and then heated under pressure with a roller having a smooth surface applied to the exterior surface of the first absorbent layer 4a and with the heating roller having a pattern of embossing projections applied to the surface of the topsheet 3. As a result, the compressed portions 10 have high-density compressed portions 10a, in which the absorbent layer and the topsheet 3 are pressed until they get almost filmy, and medium-density compressed portions 10b, in which although doesn't get filmy, the absorbent layer is of a higher density than in portions other than the compressed portion 10, between adjacent high-density compressed portions 10a. With the high-density compressed portions 10a and the medium-density compressed portions 10b alternating with each other, each compressed portion 10 forms a compressed groove where the skin surface of the sanitary napkin 1 is recessed toward the backsheet 2.

After the absorbent layer and the topsheet 3 are processed to form the compressed portions 10, the backsheet 2 is adhered beneath the first absorbent layer 4a.

In an alternative, the compressed portions 10 may be formed as a compressed groove where the exterior surface of the first absorbent layer 4a is recessed toward the skin surface, by applying the embossing projections to the exterior surface of the first absorbent layer 4a. In another alternative, the compressed portions 10 may be formed by applying the embossing projections to both the topsheet 3 and the first absorbent layer 4a.

The compressed portions 10 comprise first compressed portions 11, 11 that are disposed symmetrically about the longitudinal centerline Oy—Oy and second compressed portions 12, 12 that are disposed symmetrically about the longitudinal centerline Oy—Oy and spaced outwardly apart from the first compressed portions 11, 11. The first compressed portions 11, 11 and the second compressed portions 12, 12 are compressed grooves extending along arcuate lines that are curved toward the longitudinal centerline Oy—Oy, wherein the second compressed portions 12, 12 are spaced a constant distance apart from the first compressed portion 11, 11, all along the second compressed portions 12, 12.

In this embodiment, the first compressed portions 11, 11 function as first flexible hinges, and the second compressed portions 12, 12 function as second flexible hinges.

The compressed portions 10 also comprise lateral compressed portions 13, 13 that are connected between the first compressed portions 11, 11 at their front ends and rear ends. The lateral compressed portions 13, 13 are compressed grooves extending along arcuate lines that are curved away from the lateral reference line Ox—Ox. The lateral compressed portions 13, 13 form lateral flexible hinges. In this embodiment, the region surrounded by the first compressed portions 11, 11 and the lateral compressed portions 13, 13 is the central absorbent portion 5, and the second compressed portion 12, 12 are located outside the central absorbent portion.

The compressed portions 10 further comprise forwardly extending compressed portions 14, 14 that are extended continuously from the first compressed portions 11, 11 to project forwardly beyond the lateral compressed portion 13 and rearwardly extending compressed portions 15, 15 that are also extended continuously from the first compressed portions 11, 11 to project rearwardly beyond the lateral compressed portion. The forwardly extending compressed portions 14, 14 form forwardly extending flexible hinges, and the rearwardly extending compressed portions 15, 15 form rearwardly extending flexible hinges.

The regions between the first compressed portions 11, 11 and the second compressed portions 12, 12 are support portions 6, 6. The support portions 6, 6 are arcuate regions with a constant width all along the second compressed portions 12, 12. On the other hand, the region between the right side edge 1a and the right second compressed portion 12 and the region between the left side edge 1b and the left second compressed portion 12 are side portions 7, 7.

The absorbent layer 4 is provided to extend over the central absorbent portion 5 and the support portions 6, 6 and further extend outwardly across the second compressed portions 12, 12 halfway through the side portions 7, 7. In the central absorbent portion 5, the first absorbent layer 4a, the second absorbent layer 4b and the third absorbent layer 4c are stacked one upon another to provide a high-basis weight, bulky central absorbent layer 4A, as shown in FIG. 2. In the support portions 6, on the other hand, provided are support absorbent layers 4B, in which the first absorbent layer 4a and the second absorbent layer 4b are stacked. In the side portions 7, then, provided are side absorbent layers 4C, in which the first absorbent layer 4a and the second absorbent layer 4b are stacked.

In the absorbent layer 4, the basis weight of the central absorbent layer 4A is higher than those of the support absorbent layers 4B and the side absorbent layers 4C. Although the basis weight of the support absorbent layers 4B may be equal to that of the side absorbent layers 4C, it is preferred that the basis weight of the support absorbent layers 4B is higher than that of the side absorbent layers 4C so as to increase the stiffness of the support portions 6.

Since both sides of the support absorbent layer 4B that is in a compressed state are restricted by the first and second compressed portions 11 and 12, the density of the support absorbent layers 4B is higher than those of the central absorbent layer 4A and the side absorbent layers 4C.

Here, the first compressed portion 11 has a higher density (in both the high-density compressed portions 10a and the medium-density compressed portions 10b) than the central absorbent layer 4A and the support absorbent layer 4B that are located on both sides of the first compressed portion 11. Consequently, the first compressed portion 11 functions as the first flexible hinge which facilitates bending of the support portion 6 from the central absorbent portion 5. Likewise, the second compressed portion 12 has a higher density than the support absorbent layer 4B and the side absorbent layer 4C that are located on both sides of the second compressed portion 12, so that the second compressed portion 12 functions as the second flexible hinge which facilitates bending of the side portion 7 from the support portion 6.

As shown in FIG. 2, when the sanitary napkin 1 is flattened out and no external force is exerted thereon, h is considerably smaller than H/2, preferably h is smaller than H/6, wherein H indicates the thickness of the central absorbent portion 5 at the longitudinal centerline Oy—Oy while h indicates the height measured from the exterior surface of the backsheet 2 to the midpoint of the thickness of the first and second compressed portions 11 and 12.

As shown in FIGS. 1 and 2, the skin surface is provided at two sides thereof with leakage preventing walls 21, 21 of liquid-impermeable sheets 20, 20. The term "leakage preventing wall" as used herein refers to a portion of the liquid-impermeable sheet 20 that is folded in two with a plurality of longitudinally extending elastic members 22 bonded thereto in a stretched state. The leakage preventing walls 21, 21 are permitted to rise from the skin surface at an intermediate portion of the sanitary napkin 1, as shown in FIG. 2. At front and rear portions of the sanitary napkin 1, however, the leakage preventing walls 21, 21 are entirely bonded to the skin surface so as not to rise therefrom.

As shown in FIG. 1, the sanitary napkin 1 has the wings 18, 18 projecting outwardly from the right side edge 1a and the left side edge 1b.

The wings 18, 18 are constructed with the backsheet 2 and the liquid-impermeable sheets 20 bonded together.

On an exterior surface of the backsheet 2, there are provided a pressure-sensitive adhesive layer (not shown) for bonding a central portion of the sanitary napkin 1 to a groin piece of an undergarment and a pressure-sensitive adhesive layer (not shown) for bonding the wings 18, 18 to an outer side of the groin piece of the undergarment.

FIG. 3 shows a state where the sanitary napkin 1 is attached to a groin piece 25 of an undergarment.

The sanitary napkin 1 is centrally bonded to an inner side of the groin piece 25 through the pressure-sensitive adhesive disposed on the exterior surface of the backsheet 2. On the other hand, the wings 18, 18 are folded back against the outer side of the groin piece 25 so as to be wrapped around two side edges of the groin piece 25, whereby the wings 18, 18 are bonded to the outer side of the groin piece 25 through the pressure-sensitive adhesive.

When the undergarment is worn with the sanitary napkin 1 attached to the groin piece 25 as shown in FIG. 3 and then the distance between the wearer's thighs is reduced during daily activity, the thighs exert a compressive force F on the groin piece 25 and the sanitary napkin 1 from both sides toward the longitudinal centerline Oy—Oy. The compressive force F is transmitted to the high-density, stiff support portions 6, 6 through the second compressed portions 12, 12 and then exerted on the first compressed portions 11, 11.

Since the midpoint of the thickness of the first and second compressed portions 11 and 12 is sufficiently below the midpoint of the thickness H of the central absorbent portion 5, as shown in FIG. 2, when the compressive force F is exerted on the sanitary napkin 1, the lower portion of the central absorbent portion 5 is slightly contracted due to pressure from both sides, so that the first compressed portions 11, 11 on both sides tend to approach the longitudinal centerline Oy—Oy at a position below the central absorbent portion 5. Since the support portions 6, 6 are stiffer than the central absorbent portion 5 and are extended longitudinally of the napkin with a small width laterally of the napkin, bending of the support portions 6, 6, which might result in making the first and second compressed portions 11 and 12 approach each other, can be prevented, while the sanitary napkin 1 subjected to the compressive force can be easily bent at the first compressed portions 11, 11 and the second compressed portions 12, 12 which function as the flexible hinges.

Hence, the first compressed portions 11, 11 get further under the central absorbent layer 4A, and at the same time, the support portions 6, 6 are raised to have the first compressed portions 11, 11 closer to the wearer's crotch than the second compressed portions 12, 12, so that the central absorbent portion 5 is lifted up toward the wearer's crotch while being supported from below by the support portions 6, 6, as shown in FIG. 4. After lifted up with its width being slightly reduced and its skin surface being curved, as shown in FIG. 4, the central absorbent portion 5 is brought into close contact with the vaginal opening. Here, the central absorbent portion 5 is lifted up toward the wearer's skin over the entire length of a region held between the support portions 6, 6. Accordingly, the low-density, soft central absorbent portion 5 can be kept in close contact with the vaginal opening over a large area without causing concentration of pressure on the labia and the vaginal opening, so that the central absorbent portion 5 has a good feel when it is in close contact with the labia and the vaginal opening.

When a pressure is exerted on the central absorbent portion 5 from the wearer's body, the pressure is received by contraction of the central absorbent portion 5 and then transmitted to the support portions 6, 6 supporting the central absorbent portion 5 from below. At this time, however, the pressure can be easily relieved by cushioning effect due to elastic deformation of the support portions 6, 6 toward the undergarment and cushioning effect due to bending at the first and second compressed portions. Accordingly, even when subjected to a large pressure from the wearer's body in a state where the distance between the thighs is reduced such as in a sitting position, the sanitary napkin 1 can be easily restored to its deformed state of FIG. 4 once the pressure is relieved, thereby easily keeping close contact between the central absorbent portion 5 and the vaginal opening. Since the sanitary napkin 1 has such resiliency and cushioning effect, residual twist or distortion can be effectively prevented so as not to substantially decrease the area of the skin surface, so that menstrual blood absorption capacity can be maintained high.

Moreover, since the first compressed portions 11, 11 and the second compressed portions 12, 12 are located below the central absorbent portion 5 away from the wearer's skin. Therefore, the probability that the first compressed portions 11, 11 and the second compressed portions 12, 12, as well as the support portions 6, 6 will come into direct contact with the wearer's skin can be reduced, so that an uncomfortable feel due to their stiffness is hardly given to the wearer's body.

Furthermore, since the first compressed portions 11, 11 and the second compressed portions 12, 12 extend in the shape of a line curved toward the longitudinal centerline Oy—Oy, the first compressed portions 11, 11 and the second compressed portions 12, 12 can match curved surfaces of the thighs. Therefore, the compressive force F applied from the thighs can uniformly acts on every part of the first compressed portions 11, 11, the second compressed portions 12, 12, and the support portions 6, 6.

Still furthermore, the second compressed portions 12, 12 are spaced a constant distance apart from the first compressed portion 11, 11, and therefore, the support portions 6, 6 have a constant width. Therefore, every part of the support portions 6, 6 can function to lift up the central absorbent portion 5 toward the wearer's skin, so that the central absorbent portion 5 can easily come in close contact with vaginal opening over a long range.

As has been described hereinabove, since the sanitary napkin 1 subjected to the lateral compressive force F can be so deformed that the central absorbent portion 5 comes into close contact with the vaginal opening, the central absorbent portion 5 supported by the support portions 6, 6 can be certainly kept in close contact with the vaginal opening even when the sanitary napkin 1 is attached to a loose undergarment that exerts a relatively weak tightening force on the wearer's body.

It should be noted that the first compressed portions 11, the second compressed portions 12 and the support portions 6 are preferably curved as shown in Figures, so as to minimize the variation in distance between respective parts of the individual support portions 6, 6 and the thighs so that the compressive force F can be applied to the support portions 6, 6 as uniformly as possible. However, a similar effect can be obtained as long as the first compressed portions 11, the second compressed portions 12 and the support portions 6 approach each other the nearest at the lateral centerline Ox—Ox and extend away from the longitudinal centerline Oy—Oy as they extend longitudinally away from the lateral centerline Ox—Ox. The compressed portions 11, 12 and the support portions 6, 6 may extend in the shape of an arc of a circle or ellipse, a trapezoid or a "V", for example. The first compressed portions 11 and the second compressed portions 12 may extend in the shape of a zigzag line or wavy line, as long as they approach each other the nearest at the lateral centerline Ox—Ox and extend away from the longitudinal centerline Oy—Oy as they extend longitudinally away from the lateral centerline Ox—Ox.

FIG. 5 shows a deformed state of the sanitary napkin 1 at the time of wearing a tight undergarment which can exert a large tightening force on the wearer's body and is suitable for use during menstruation. In an undergarment of this kind, an elastic band 25B is disposed to extend from a groin piece 25A to a back body, so that a central portion of the groin piece 25A is lifted up along the cleft of the wearer's buttocks. In this case, therefore, the central absorbent portion 5 is also lifted up toward the vaginal opening due to the lifting force exerted by the undergarment. At this time, since the support portions 6, 6 between the first compressed portions 11, 11 and the second compressed portions 12, 12 are relatively free, the sanitary napkin 1 can be easily deformed so that the support portions 6, 6 approach each other as the central absorbent portion 5 is lifted up.

Accordingly, when a lifting force is applied to the central absorbent portion 5 from the groin piece 25A of the undergarment, the sanitary napkin 1 can be easily deformed in response to the force. As a result, the sanitary napkin 1 can comfortably contact the wearer's body and can be easily felt as an integral part of the undergarment.

In the sanitary napkin 1, since the lateral compressed portions 13, 13 are provided as lateral flexible hinges to facilitate bending, the whole central absorbent portion 5 surrounded by the first compressed portions 11, 11 and the lateral compressed portions 13, 13 can be easily lifted up toward the wearer's body, as shown in FIGS. 4 and 5.

In the sanitary napkin 1, moreover, the laterally spaced apart, forwardly extending compressed portions 14, 14 are provided in the front portion, while the laterally spaced apart, rearwardly extending compressed portions 15, 15 are provided in the rear portion. These compressed portions can also function as flexible hinges. Therefore, the front and rear portions of the sanitary napkin 1 can be deformed three-dimensionally more easily to conform to the mons pubis and the buttocks.

Menstrual blood discharged from the vaginal opening is mainly applied to the central absorbent portion 5 that is in close contact with the vaginal opening and is passed through the topsheet 3 and then absorbed by the central absorbent layer 4A. Since the central absorbent portion 5 is surrounded by the first compressed portions 11, 11 and the lateral compressed portions 13, 13, outward diffusion of menstrual blood can be easily prevented by these compressed portions, so that the menstrual blood can be diffused in and absorbed by the central absorbent portion 5, thereby fully exploiting the liquid absorption capacity of the central absorbent layer 4A.

Here, although menstrual blood flowing along the topsheet 3 may possibly reach the support portions 6, 6 and the side portions 7, 7, such menstrual blood can also be absorbed in the support portions 6, 6 and the side portions 7, 7 since they have the absorbent layers. It should be noted that the support absorbent layer 4B in the support portion 6 defined between the first and second compressed portions 11 and 12 is confined between the backsheet 2 and the topsheet 3 to have a relatively small cross section. Therefore, even after the support absorbent layers 4B, 4B are wetted by absorption of menstrual blood, the density of the support absorbent layers 4B, 4B can be kept high, while preventing its strength from decreasing. Hence, the stiffness and the cushioning effect for supporting the central absorbent portion 5 from below can be maintained even after the support absorbent layers 4B, 4B are wetted, so that the sanitary napkin 1 can be prevented from being crushed and flattened by the pressure applied from the wearer's body.

When the sanitary napkin 1 as attached to the groin piece 25 is deformed to conform to the wearer's crotch, moreover, the leakage preventing walls 21, 21 rise up so that their upper ends can come into contact with the wearer's crotch, as shown in FIGS. 4 and 5. Lateral leakage of menstrual blood can also be prevented by these leakage preventing walls 21, 21.

Hereinbelow, preferred values for the individual components will be described. Also in other embodiments that will be described later, it is preferred that the portions having the same construction as those in the first embodiment are of similar values. Hereinbelow, although the absorbent layer is constructed by wrapping fibers in a hydrophilic paper or the like, the density and basis weight of the absorbent layer are measured without the hydrophilic paper or the like.

Preferably, the central absorbent layer 4A is of a large liquid absorption capacity so as to be able to absorb menstrual blood sufficiently in the central absorbent portion 5. Also preferably, it is soft to the touch and so resilient as to be able to restore its thickness when a pressure exerted thereon from the wearer's body is relieved.

The central absorbent layer 4A preferably has a density in the range of 0.05 to 0.15 $g/cm^3$, more preferably in the range of 0.05 to 0.125 $g/cm^3$, and most preferably in the range of 0.05 to 0.1 $g/cm^3$. If within this range, it can feel soft when in contact with the vaginal opening and it can be highly resilient against pressure from above. The central absorbent layer 4A preferably has a basis weight from 400 to 1200 $g/m^2$, more preferably, from 500 to 1000 $g/m^2$. If within this range, sufficient liquid absorption capacity can be obtained, and sufficient resiliency against pressure from above can be realized in cooperation with the density in the above-mentioned preferred range.

The central absorbent portion 5 may be constructed to include a liquid guide layer such as through-air bonded nonwoven fabric between the topsheet 3 and the central absorbent layer 4A, so that menstrual blood having passed through the topsheet 3 passes through the liquid guide layer before absorption by the central absorbent layer 4A. In this case, the preferred density range refers to the density of the absorbent layer exclusive of the liquid guide layer, while the preferred basis weight refers to that of the absorbent layer inclusive of the liquid guide layer.

The width W1 of the central absorbent portion 5 at the lateral reference line Ox—Ox depends on the width of the female genital organ. Since the crotch width of average women is about 30 mm, the width W1 of the central absorbent portion 5 is preferably in the range of 15 to 50 mm, more preferably in the range of 20 to 40 mm.

The support absorbent layer 4B has a higher density than the central absorbent layer 4A and the side absorbent layer 4C. If the separation distance between the first and second compressed portions 11 and 12 is sufficiently small, the density of the support absorbent layer 4B can be increased during the process of forming the first and second compressed portions 11 and 12. The density of the support absorbent layer 4B may be increased by compression prior to the formation of the first and second compressed portions 11 and 12.

The density of the support absorbent layer 4B is preferably in the range of 0.1 to 0.5 g/cm$^3$. In order that the support absorbent layers 4B are stiff enough to lift up and support the central absorbent portion 5, the lower limit of the density is preferably 0.125 g/cm$^3$, more preferably 0.15 g/cm$^3$.

In the case where excellent cushioning effect is expected in the support absorbent layer 4B, on the other hand, the upper limit of the density is preferably 0.2 g/cm$^3$.

In the case where the central absorbent layer 4A has a high basis weight and a sufficient cushioning effect, the density of the support absorbent layer 4B may be in the range of 0.2 to 0.5 g/cm$^3$ in consideration of the effect of supporting the central absorbent portion 5 from below. In the case where the support portion is entirely formed as the compressed portion, as will be described later with reference to FIG. 10, the density of the whole compressed portion is in the range of 0.5 to 1.5 g/cm$^3$.

The basis weight of the support absorbent layer 4B is preferably from 300 to 800 g/m$^2$, more preferably from 350 to 600 g/m$^2$. This basis weight is preferably lower than that of the central absorbent layer 4A but higher than that of the side absorbent layer 4C. Here, the sum W2 of the width of the support portion 6, the width of the first compressed portion 11 and the width of the second compressed portion 12 is preferably in the range of 5 to 15 mm, more preferably in the range of 5 to 10 mm. When an ordinary undergarment is worn, clearance of about 5 mm will be left between a groin piece of the undergarment and the wearer's vaginal opening, but if the width W2 is set in the range of 5 to 15 mm, preferably in the range of 5 to 10 mm, as set forth above, the central absorbent portion 5 can be kept in close contact with the vaginal opening in the deformed state of FIGS. 4 and 5.

Figure 13:
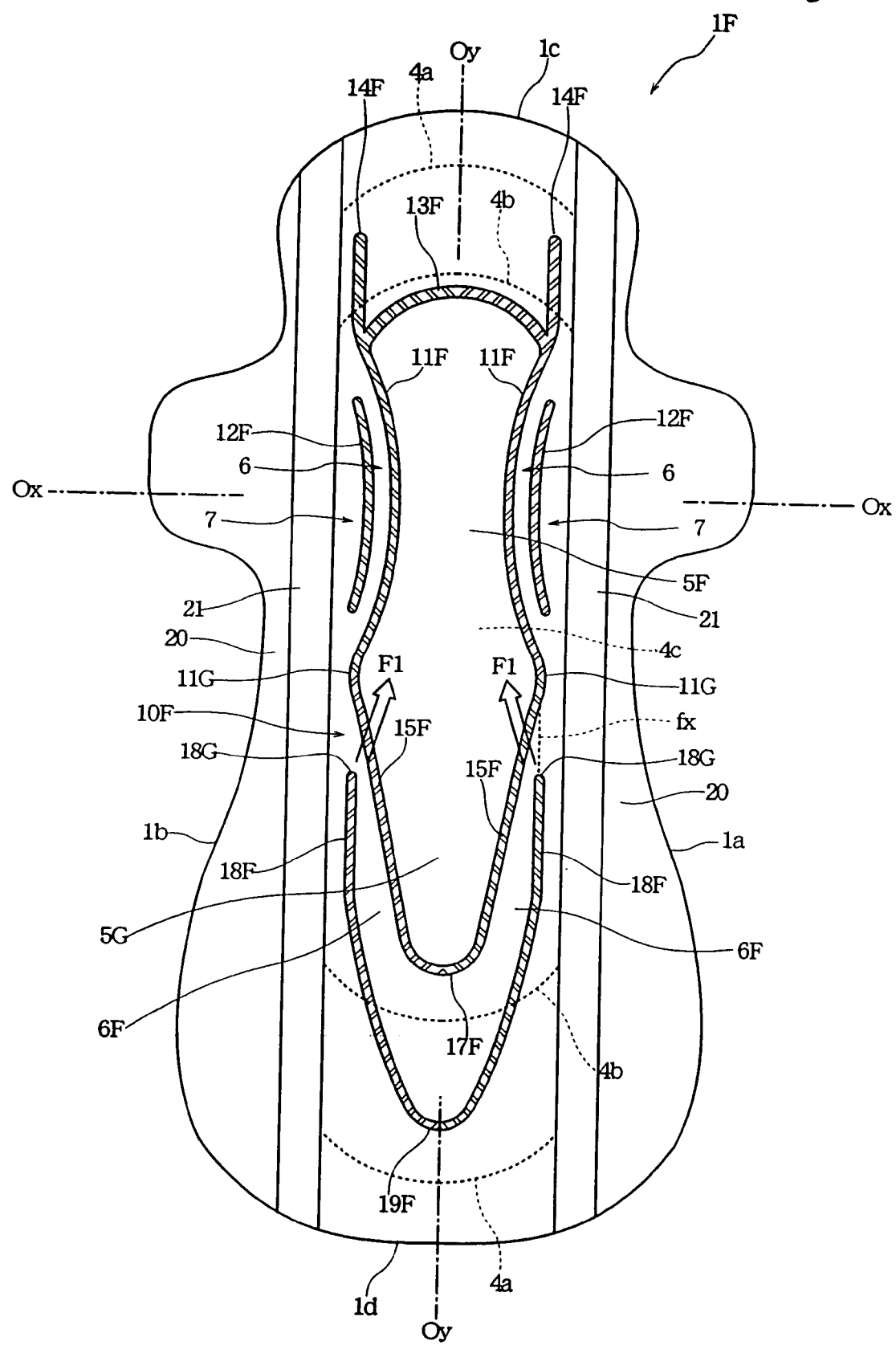
FIG. 13 is a top plan view showing a sanitary napkin according to a seventh embodiment of the present invention.

The length (dimension measured in parallel with the longitudinal centerline Oy—Oy) of the support portions 6, 6 depends on the length of the second compressed portions 12, 12. If the length of the support portions 6, 6 is too short, the central absorbent portion 5 cannot be strongly pushed up toward the vaginal opening. Accordingly, the length of the support portions 6, 6 is preferably at least 30 mm. On the other hand, the upper limit of the length is preferably 100 mm. However, in case of long-type sanitary napkins for night-time use or heavy menstrual bleeding such as shown in FIG. 13, the length of the support portions 6, 6 may be in excess of 100 mm. For example, when the sanitary napkin is the long type having a length of about 380 mm, the upper limit of the length of the support portions 6, 6 is about 120 mm. If the length is in excess of 100 mm (in excess of 120 mm in case of the long type), the sanitary napkin 1 may possibly feel stiff against the wearer's body.

The side absorbent layers 4C have a density in the range of 0.05 to 0.15 g/cm$^3$, which may be equal to that of the support portions 6, 6 or that of the central absorbent layer 4A. In order that when the right-hand side portion 7 and the left-hand side portion 7 approach each other due to the compressive force F applied to both sides of the sanitary napkin 1, as shown in FIGS. 4 and 5, the exerted force can be certainly transmitted to the second compressed portions 12, 12 so that the support portions 6, 6 can lift up the central absorbent portion 5, the density of the side absorbent layers 4C is preferably equal to or higher than that of the central absorbent layer 4A, and the width W3 of the side absorbent layers 4C is preferably from 10 to 35 mm, more preferably from 10 to 20 mm. Moreover, it is preferred that the basis weight of the side absorbent layers 4C is about 300 to 450 g/m$^2$. The upper limit of the basis weight should not be limited to the above-mentioned range, but may be 600 g/m$^2$ in case of sanitary napkins, for example.

In the first and second compressed portions 11, 12 of the compressed portions 10, it is preferred that the density of the most densified portions (i.e., the high-density compressed portions 10a) is sufficiently higher than those of the central absorbent layer 4A, the support absorbent layers 4B and the side absorbent layers 4C. The density of the high-density compressed portions 10a is preferably in the range of 0.5 to 1.5 g/cm$^3$. Here, the density of the medium-density compressed portions 10b in the compressed portions 10 need not be set in the above-mentioned range, because the flexible hinges can be formed of the high-density compressed portions 10a. In order to facilitate bending at the flexible hinges, however, it is also preferred to set the density of the medium-density compressed portions 10b in the above-mentioned range. In order that the first compressed portions 11, 11 and the second compressed portions 12, 12 can function as the flexible hinges, it is also preferred that the width W4 is in the range of 1.5 to 3 mm.

Next, preferred materials for the individual components will be described.

For the topsheet 3, a synthetic resin film formed with a large number of liquid passage holes, a synthetic resin film formed in the shape of a net or a through-air bonded nonwoven fabric of chemical fibers may be used. In an alternative, a composite material, in which the synthetic resin film having the liquid passage holes appears on the skin surface and the through-air bonded nonwoven fabric is laid beneath it, may be used. In this case, the synthetic resin film is formed of polyethylene resin containing titanium oxide as a whitening agent, while the through-air bonded nonwoven fabric is formed of sheath/core bicomponent synthetic fibers of which the core component is polyethylene terephthalate (PET) containing titanium oxide and the sheath component is polyethylene (PE), the sheath/core bicomponent synthetic fibers being thermally fusion-bonded together by means of hot air.

It is also possible to use different nonwoven fabrics such as spunlaced nonwoven fabric, spunbonded nonwoven fabric and the like for the topsheet 3.

The backsheet 2 is a liquid-impermeable, breathable sheet such as a polyethylene (PE) or polypropylene (PP) film formed with minute pores. The minute pores may be appropriately distributed over the film for improving breathability such as by adding inorganic filler such as $CaCO_3$ and $BaSO_4$ to the plastic film, followed by drawing. The film may have a thickness of about 15 to 50 µm. In an alternative, a material in which a thermoplastic resin is laminated to a nonwoven fabric may be used.

The first absorbent layer 4a, the second absorbent layer 4b and the third absorbent layer 4c are formed by accumulating pulp such as ground pulp, mercerized pulp or crosslinked pulp. After stacked one upon another, the absorbent layers 4a, 4b and 4c are entirely wrapped in a hydrophilic paper. The pulp may be mixed with synthetic absorbent polymer such as polyacrylate, polyacrylamide and maleic anhydride or natural absorbent polymer such as starch and cellulose. In an alternative, absorbent polymer in the form of sheet may be contained therein.

Particularly in the case where the absorbent polymer, which may be in the form of sheet, is contained in the support portions 6, 6, the bonding strength between pulp can be increased when they are wetted by absorption of menstrual blood, thereby increasing the stiffness of the support portions 6, 6.

For the liquid-impermeable sheets 20 for forming the leakage preventing walls 21, a spunbonded nonwoven fabric, a meltblown nonwoven fabric or a laminate thereof may be used. Preferably, the sheets 20 are treated to be water-repellent.

In appropriate portions but for the compressed portions 10, the backsheet 2, the topsheet 3, the absorbent layer 4 and the liquid-impermeable sheets 20 are bonded to each other through an adhesive.

In the followings, other embodiments of the present invention will be described. Hereinafter, the detailed description of the portions having the same construction as those of the first embodiment will be omitted by designating them by the common reference numerals.

Figure 6:
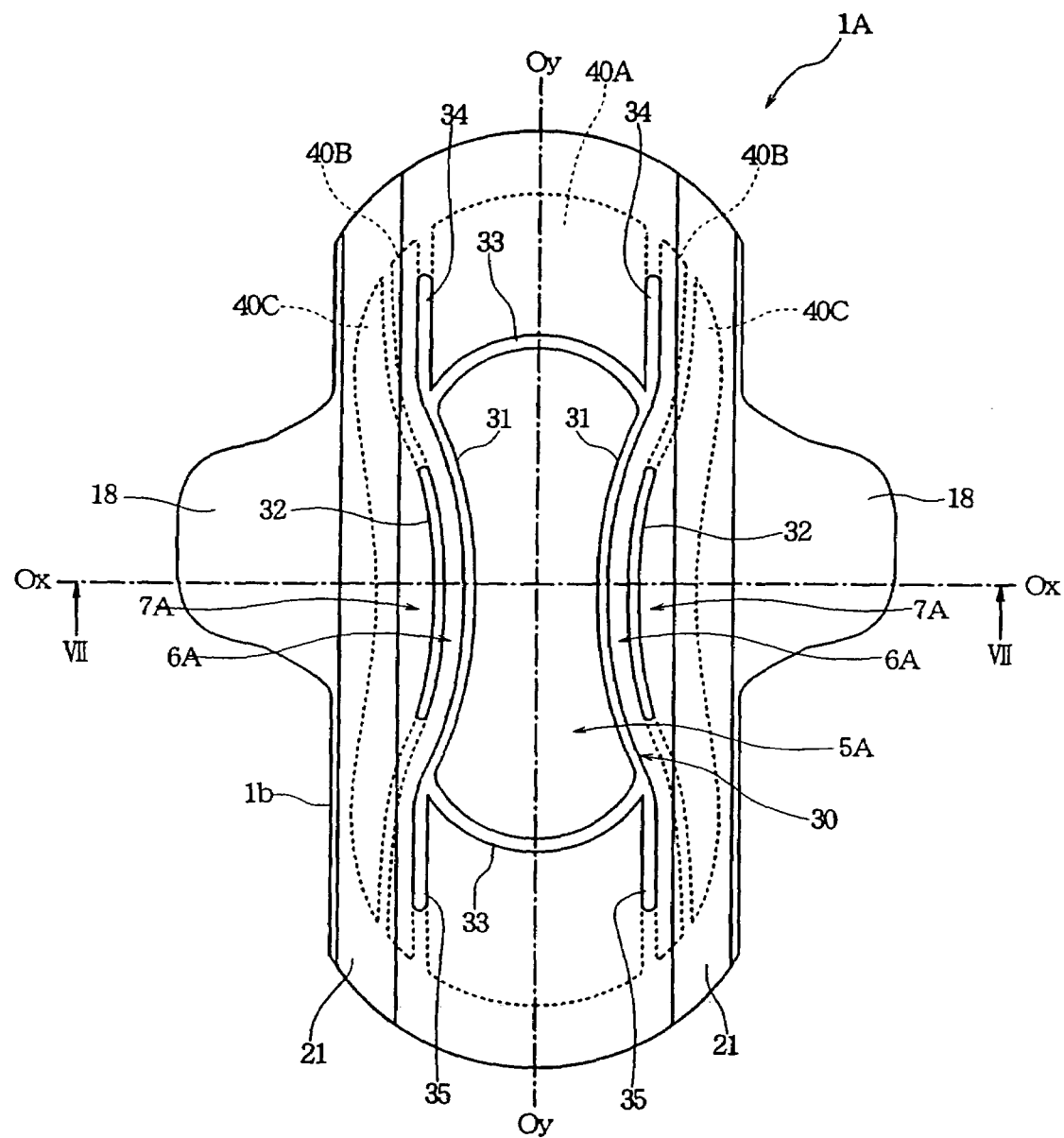
FIG. 6 is a top plan view showing a sanitary napkin according to a second embodiment of the present invention.
Figure 7:
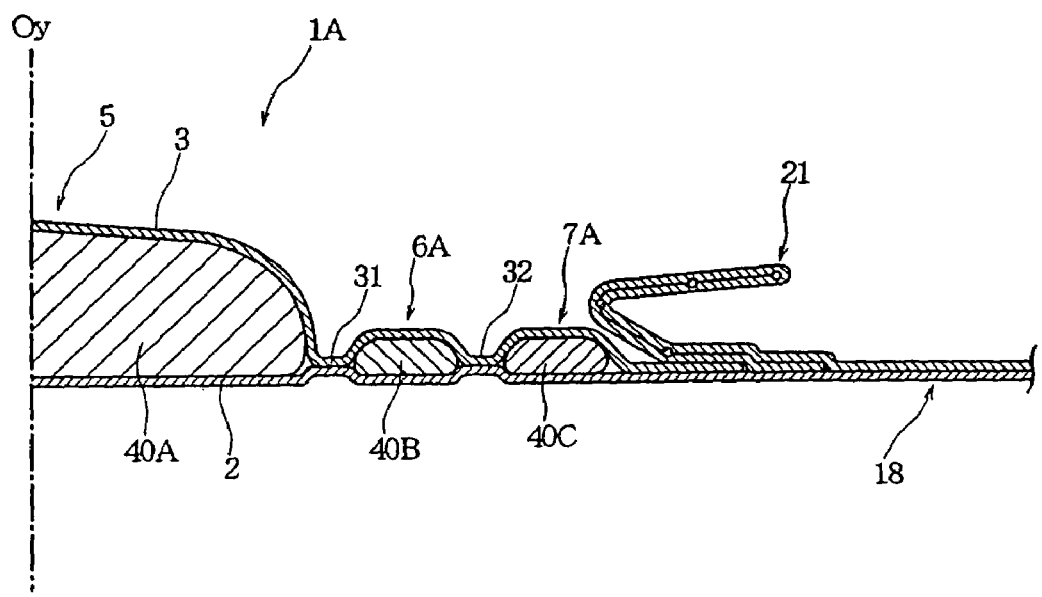
FIG. 7 is a half sectional view of the sanitary napkin taken along line VII—VII of FIG. 6.

FIG. 6 is a top plan view showing a sanitary napkin 1A according to a second embodiment of the present invention, and FIG. 7 is a half sectional view of the sanitary napkin 1A taken along line VII—VII of FIG. 6.

In this embodiment, separate absorbent layers, i.e., a central absorbent layer 40A, support absorbent layers 40B, 40B, and side absorbent layers 40C, 40C are held between the backsheet 2 and the topsheet 3.

Preferred density ranges and basis weight ranges of the individual absorbent layers 40A, 40B and 40C are identical to those in the first embodiment.

At locations between the central absorbent layer 40A and the support absorbent layers 40B, the backsheet 2 and the topsheet 3 are directly bonded together to form first bonded portions 31, 31, forwardly extending bonded portions 34, 34 and rearwardly extending bonded portions 35, 35. Also at locations between the support absorbent layers 40B and the side absorbent layers 40C, the backsheet 2 and the topsheet 3 are directly bonded together to form second bonded portions 32, 32. At locations forwardly and rearwardly spaced apart from the lateral reference line Ox—Ox, lateral compressed portions 33, 33 are connected between the first bonded portions 31, 31. In the lateral compressed portions 33, 33, the central absorbent layer 40A is compressed together with the topsheet 3.

The bonded portions and the compressed portions are formed to extend in a similar pattern to the compressed potions 10 of FIG. 1. That is, the region between the right first bonded portion 31 and the left first bonded portion 31 is a central absorbent portion 5A, the regions between the right first bonded portion 31 and the right second bonded portion 32 and between the left first bonded portion 31 and the left second bonded portion 32 are support portions 6A, 6A, and the regions between the right second bonded portion 32 and the right side edge 1a and between the left second bonded portion 32 and the left side edge 1b are side portions 7A, 7A.

Since the first bonded portions 31, 31 can function as the first flexible hinges, and the second bonded portions 32, 32 can function as the second flexible hinges, the sanitary napkin 1A of FIGS. 6 and 7 can be deformed as shown in FIGS. 4 and 5 when subjected to a lateral compressive force.

Figure 8A:
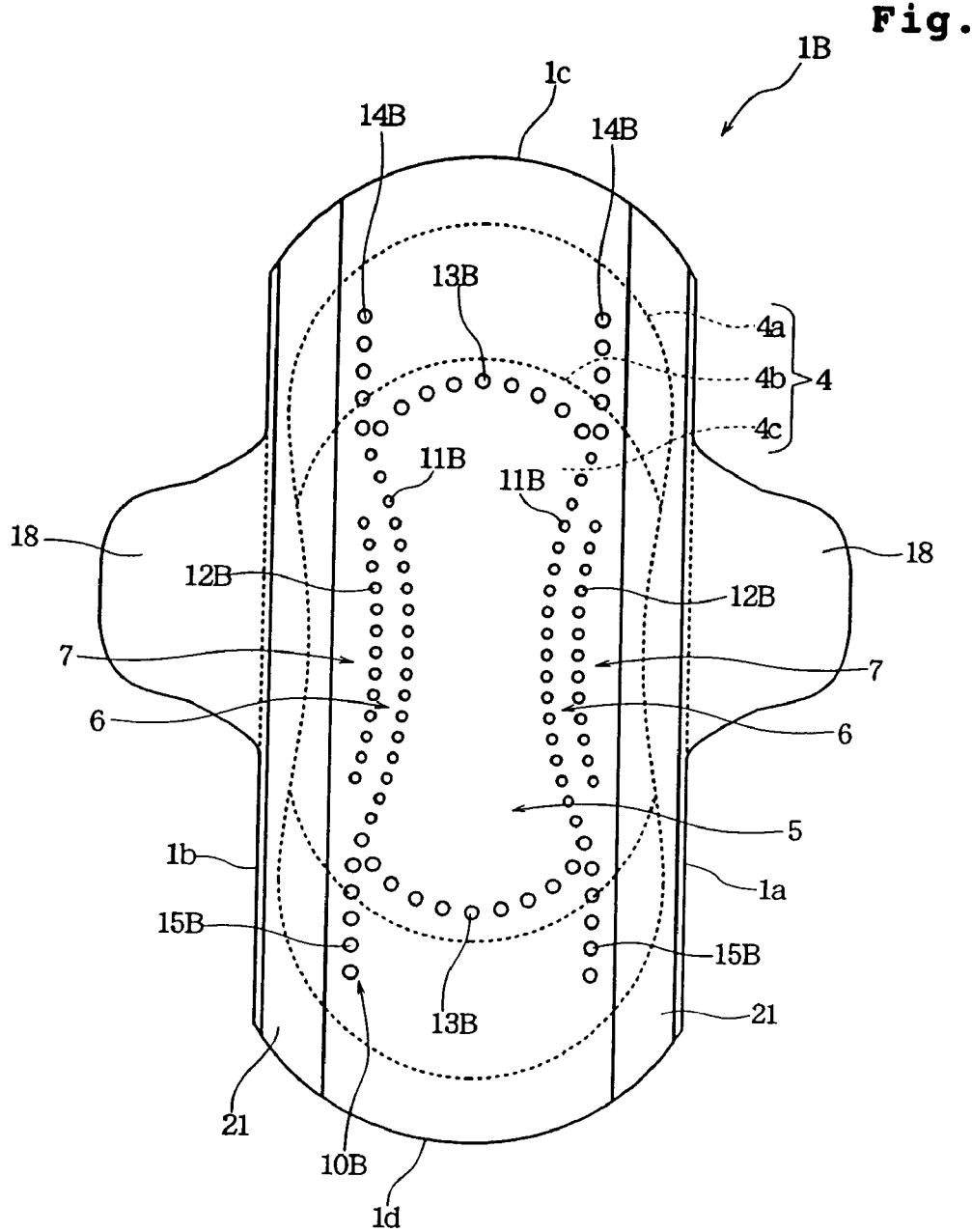
FIG. 8A is a top plan view showing a sanitary napkin according to a third embodiment of the present invention.

FIG. 8A is a top plan view showing a sanitary napkin 1B according to a third embodiment of the present invention.

In the sanitary napkin 1B, compressed portions 10B are formed in a similar pattern to the compressed potions 10 of FIG. 1. The compressed portions 10B comprise first compressed portion 11B, 11B, second compressed portions 12B, 12B, lateral compressed portions 13B, 13B, forwardly extending compressed portions 14B, 14B and rearwardly extending compressed portions 15B, 15B. However, the compressed portions 10B are not formed as continuously extending compressed grooves but as compressed dots that are arranged at spaced intervals along the pattern.

The compressed portions 10B are formed such that the topsheet 3 and the absorbent layer 4 are heated under pressure only at the dots to have a high density. It should be noted that neither heat nor pressure is applied to locations between adjacent compressed dots when these compressed dots are formed with embossing projections of a dot pattern.

Also in the sanitary napkin 1B, since the first compressed portions 11B, 11B can function as the first flexible hinges and the second compressed portions 12B, 12B can function as the second flexible hinges, such a deformation as shown in FIGS. 4 and 5 can be realized.

Figures 8B, 8C:
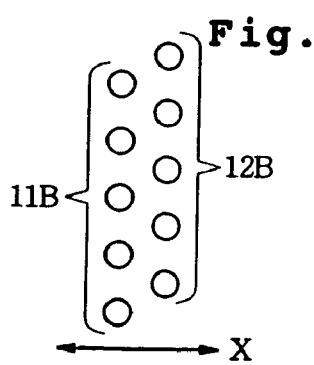
FIGS. 8B and 8C are enlarged top plan views showing the shape of compressed dots.

The compressed dots may be in a circular shape, as shown in FIGS. 8A and 8B, or the compressed dots may be in the shape of a longitudinally elongated short line, as shown in FIG. 8C. Preferably, the compressed dots constituting the first compressed portions 11B and the compressed dots constituting the second compressed portions 12B are staggered so that intermediate portions that are left uncompressed and unheated between adjacent compressed dots of the first compressed portions 11B do not overlap laterally (in the X-direction) with intermediate portions that are left uncompressed and unheated between adjacent compressed dots of the second compressed portions 12B, as shown in FIGS. 8B and 8C.

With the compressed dots being thus staggered, when menstrual blood applied to the central absorbent portion 5 is laterally diffused along the topsheet 3 and the absorbent layer, the compressed dots can function as a labyrinth against the lateral migration of the menstrual blood, effectively inhibiting the menstrual blood from migrating to the side portions 7, 7.

Here, one of the first and second compressed portions may be formed as compressed grooves like the compressed portions 10 of FIG. 1, while the other may be formed as rows of compressed dots, as shown in FIGS. 8A, 8B and 8C. For example, it is possible that the first compressed portions, the lateral compressed portions, the forwardly extending compressed portions and the rearwardly extending compressed portions are all formed as compressed grooves, while only the second compressed portions are formed as rows of compressed dots. It is also possible that the second compressed portions are formed as compressed grooves, while the first compressed portions are formed as rows of compressed dots wholly or only at regions confronted by the second compressed portions. In these cases, the lateral compressed portions, the forwardly extending compressed portions and the rearwardly extending compressed portions may be formed either as compressed grooves or as rows of compressed dots.

However, it is preferred that the first compressed portions closer to the longitudinal centerline Oy—Oy are formed as compressed grooves while the second compressed portions are formed as rows of compressed dots. In this case, the menstrual blood applied to the central absorbent portion 5 can be prevented from migrating to the support portions 6, 6, so that deterioration of stiffness or strength of the support portions 6, 6 can be certainly inhibited.

In the case where the compressed portions are formed as rows of compressed dots, as set forth above, since uncompressed portions between adjacent compressed dots facilitate bending in the longitudinal direction, the front and rear portions of the sanitary napkin can easily be bent and deformed to conform to the abdomen and buttocks, respectively. Particularly when the compressed dots are staggered, as shown in FIGS. 8B and 8C, the effect of bending can be enhanced without increasing the bending stiffness of the compressed portions.

In the case where short line-shaped compressed dots are formed, as shown in FIG. 8C, it is preferred that the short line-shaped compressed dots have a length of about 10 to 20 mm and intermediate portions (uncompressed portions) between short line-shaped compressed dots adjacent each other in the longitudinal direction have a length of about 5 to 10 mm. Here, the individual short line-shaped compressed dots may be formed by alternating the high-density compressed portions 10a with the medium-density compressed portions 10b. The compressed portions shown in FIG. 1 may be interrupted at an arbitrary position.

Figure 9:
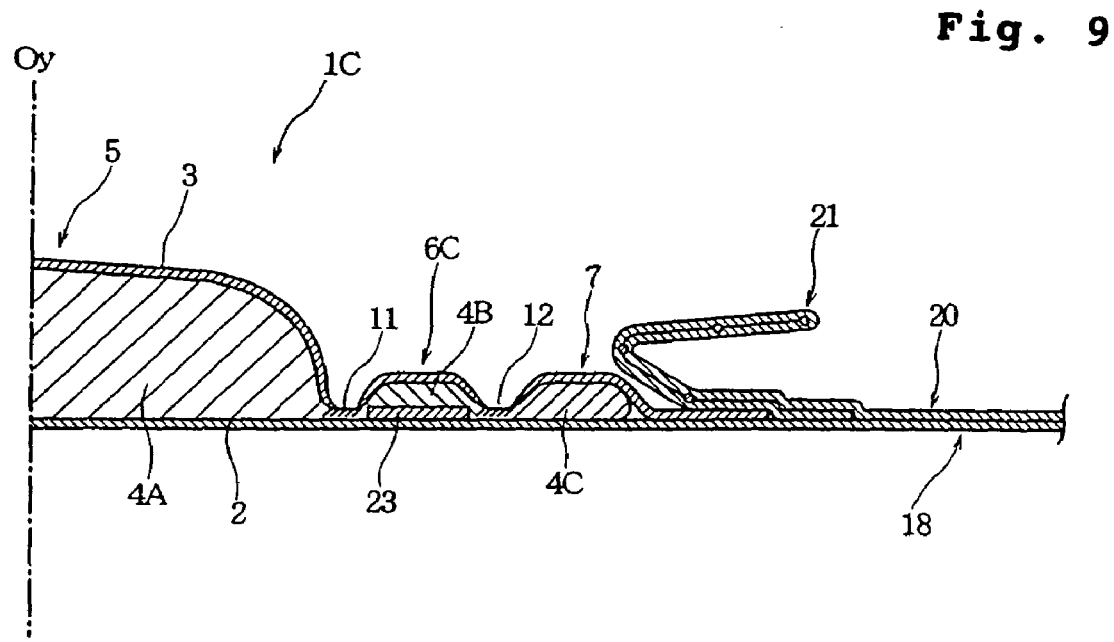
FIG. 9 is a half sectional view showing a sanitary napkin according to a fourth embodiment of the present invention.

FIG. 9 is a half sectional view showing a sanitary napkin 1C according to a fourth embodiment of the present invention.

The structure of the sanitary napkin 1C is similar to that of FIG. 1, except that reinforcing members 23 are provided in support portions 6C, 6C together with the support absorbent layers 4B, 4B. The reinforcing members 23 have a higher density and a higher stiffness than the central absorbent layer 4A and the side absorbent layers 4C, and for example, may be a foamed resin material, a cardboard material, or an air-laid nonwoven fabric in which pulp and synthetic fibers are thermally fusion-bonded together or fixed together with a binder. With the reinforcing members 23 thus provided, the stiffness of the support portions 6C can be increased, so that the central absorbent portion 5 can be certainly supported from below, thereby keeping the central absorbent portion 5 in close contact with the vaginal opening.

It is also possible to provide only the reinforcing members 23 in the support portions 6C, without providing the support absorbent layers 4B.

The reinforcing members 23 may be provided between the backsheet 2 and the topsheet 3 or adhered to the exterior surface of the backsheet 2.

Figure 10:
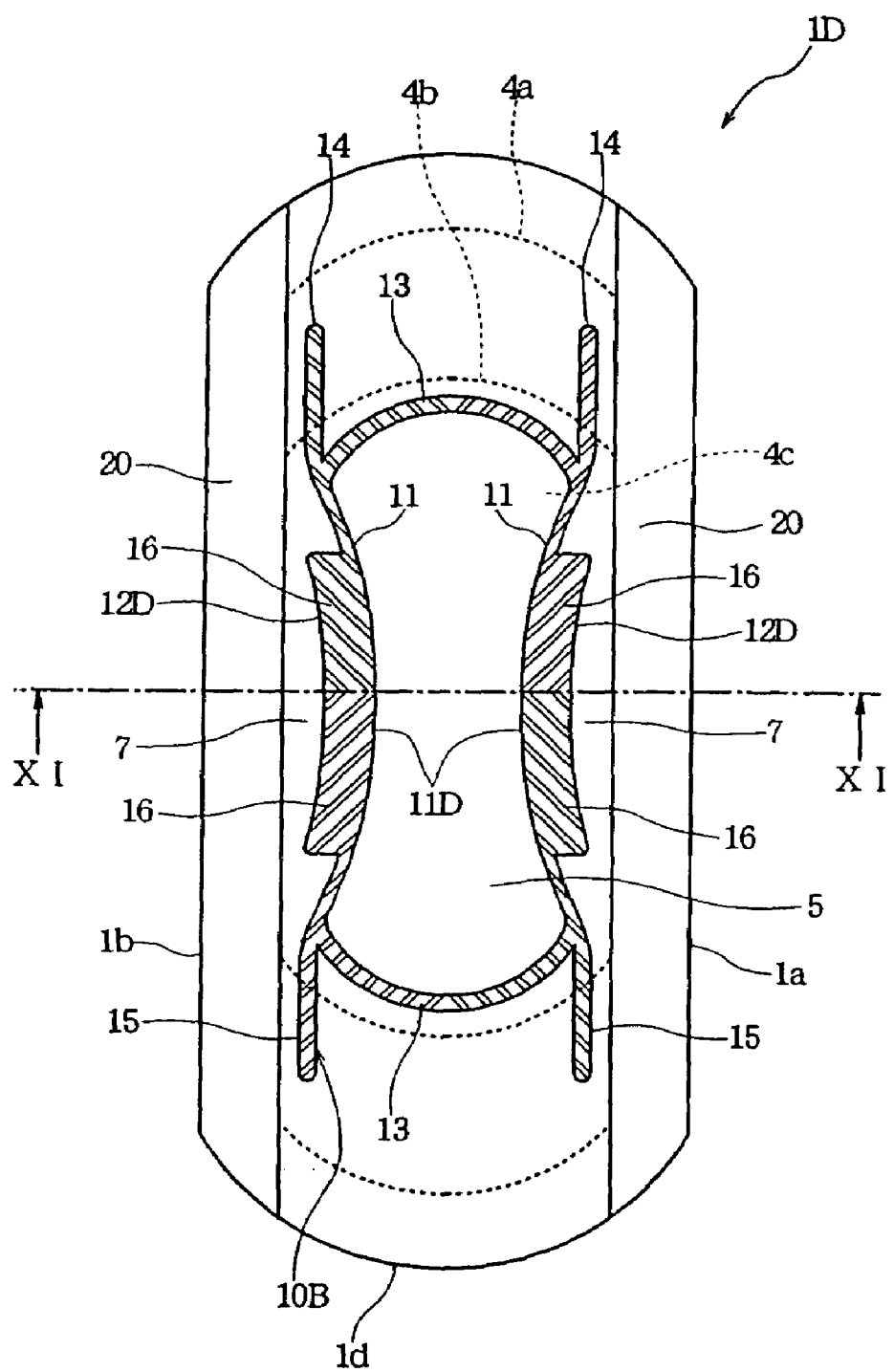
FIG. 10 is a top plan view showing a sanitary napkin according to a fifth embodiment of the present invention.
Figure 11:
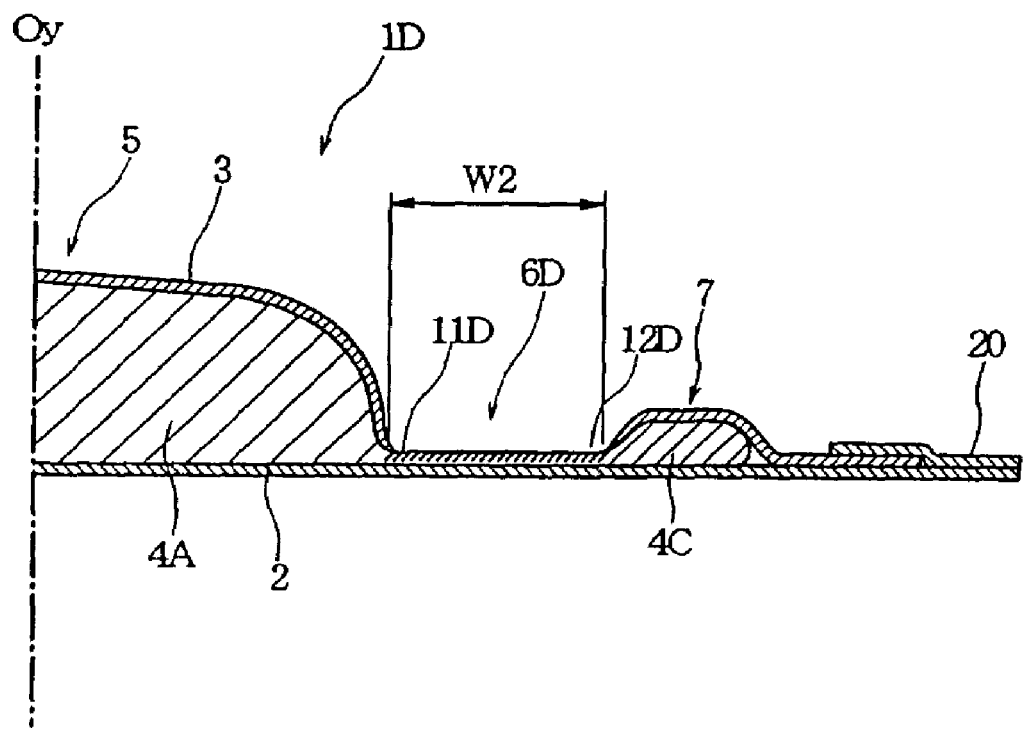
FIG. 11 is a half sectional view of the sanitary napkin taken along line XI—XI of FIG. 10.

FIG. 10 is a top plan view showing a sanitary napkin 1D according to a fifth embodiment of the present invention, and FIG. 11 is a half sectional view taken along line XI—XI of FIG. 10.

In the sanitary napkin 1D, part of the first compressed portions 11, 11 are widened toward the right side edge 1a and the left side edge 1b and integrated into the second compressed portions 12, 12, thereby forming wide compressed portions 16, 16. These compressed portions 16, 16 are support portions 6D, 6D. The width W2 of the compressed portions 16, 16 is sufficiently larger than those of the other compressed portions. The width W2 is preferably in the range of 5 to 15 mm, more preferably in the range of 5 to 10 mm, as in the first embodiment.

In the individual support portions 6D of the sanitary napkin 1D, therefore, the topsheet 3 and the absorbent layer 4 are highly compressed, so that a boundary line between the support portion 6D and the central absorbent portion 5 becomes a first flexible hinge 11D in the shape of an arcuate line while a boundary line between the support portion 6D and the side portion 7 becomes a second flexible hinge 12D in the shape of an arcuate line. When subjected to the compressive force F, the support portions 6D, 6D rise up to bring the central absorbent portion 5 into close contact with the vaginal opening in the same manner as shown in FIGS. 4 and 5. The high-density support portions 6D, 6D are highly stiff, but the stiff support portions 6D, 6D hardly give an uncomfortable feel to the wearer's crotch because they can get under the central absorbent portion 5 away from the wearer's crotch during wear, as shown in FIGS. 4 and 5.

It should be noted that although the sanitary napkin 1D of FIGS. 10 and 11 does not have either the wings 18, 18 or the leakage preventing walls 21, 21, the sanitary napkin 1D is also used with the exterior surface of the backsheet 2 being adhered to the inner side of the groin piece 25 of the undergarment through a pressure-sensitive adhesive layer. When pressed by the thighs, then, the central absorbent portion 5 can be pressed against the vaginal opening, as shown in FIGS. 4 and 5.

Referring to FIG. 12 through FIG. 16, yet other embodiments will be described hereinbelow. The flexible hinges in the first through fifth embodiments are formed in the same or similar pattern, but flexible hinges in the embodiments shown in FIG. 12 through FIG. 16 are formed in patterns different from that of the first through fifth embodiments.

Regarding the constructions but for the patterns of the flexible hinges, however, the constructions shown in the first through fifth embodiments may, of course, be selectively adopted for the embodiments shown in FIG. 12 through FIG. 16. Hereinbelow, therefore, described will be only the difference in pattern of the flexible hinges, while the detailed description of the other portions will be omitted by designating them by the reference numerals common to the individual embodiments.

Figure 12:
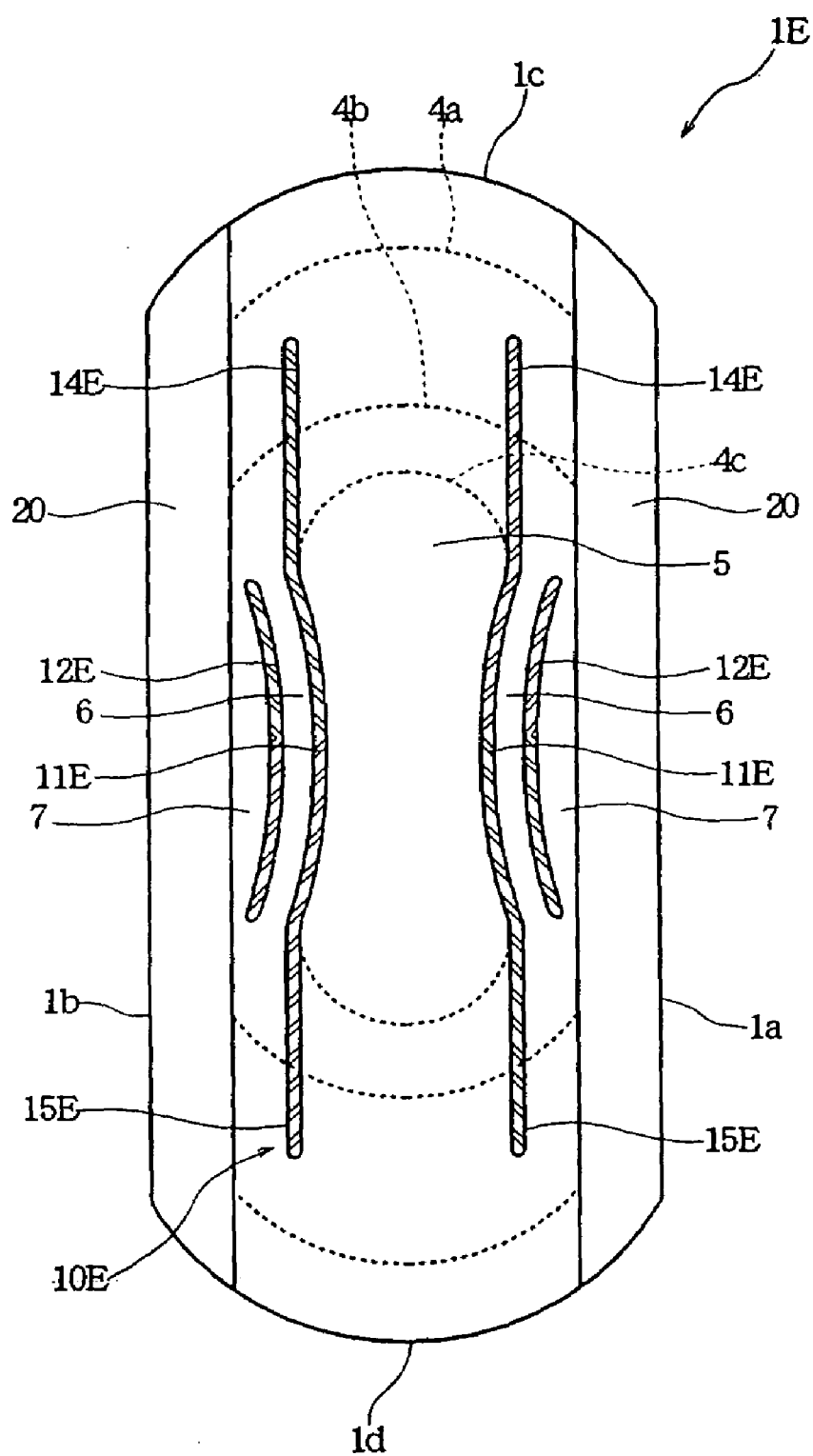
FIG. 12 is a top plan view showing a sanitary napkin according to a sixth embodiment of the present invention.

FIG. 12 is a top plan view showing a sanitary napkin 1E according to a sixth embodiment of the present invention.

Compressed portions 10E provided in the sanitary napkin 1E of FIG. 12 do not include the lateral compressed portions 13, 13 of FIG. 1, so that forwardly extending compressed portions 14E, 14E and rearwardly extending compressed portions 15E, 15E are continuously extended forwardly and rearwardly from first compressed portions 11E, 11E in the shape of an arcuate line. The region between the first compressed portions 11E, 11E is the central absorbent portion 5. Second compressed portions 12E, 12E are disposed outside the central absorbent portion 5.

The second compressed portions 12E, 12E are also formed in the shape of an arcuate line and spaced a constant distance apart from the first compressed portions 11E, 11E.

Also in this embodiment, the central absorbent portion 5 can be lifted up and pressed against the vaginal opening by the support portions 6, 6 in the deformed state of FIGS. 4 and 5. In addition, since menstrual blood applied to the absorbent layer can diffuse from the central absorbent portion 5 between the first compressed portions 11E, 11E into the portion between the forwardly extending compressed portions 14E, 14E and the portion between the rearwardly extending compressed portions 15E, 15E, the length of the sanitary napkin 1E can be fully exploited when a large amount of menstrual blood is applied.

FIG. 13 is a top plan view showing a sanitary napkin 1F according to a seventh embodiment of the present invention.

The sanitary napkin 1F is elongated and its width between the right side edge 1a and the left side edge 1b is increased at its rear portion to provide what is called hip-guard.

In the sanitary napkin 1F, the first absorbent layer 4a, the second absorbent layer 4b and the third absorbent layer 4c are also elongated, and the region surrounded by compressed portions provides a central absorbent portion 5F and a rear central absorbent portion 5G that is integral with the central absorbent portion 5F.

In the sanitary napkin 1F, first compressed portions 11F, 11F are formed to extend over a region, on both sides of which the wings 18, 18 are provided, and second compressed portions 12F, 12F are formed to extend outside the first compressed portions 11F, 11F. The first compressed portions 11F, 11F function as the first flexible hinges, and the second compressed portions 12F, 12F function as the second flexible hinges. In this embodiment, more specifically, the individual first compressed portions 11F, 11F are formed to extend symmetrically about the lateral reference line Ox—Ox in the shape of an arcuate line that is curved toward the longitudinal centerline Oy—Oy. The regions between the first compressed portions 11F, 11F and the second compressed portions 12F, 12F are the support portions 6, 6, while the regions outside the second compressed portions 12F, 12F are the side portions 7, 7.

In the front portion of the sanitary napkin 1F, moreover, a lateral compressed portion 13F is connected between the first compressed portions 11F, 11F, and forwardly extending compressed portions 14F, 14F are formed to project forwardly beyond the lateral compressed portion 13F.

In this embodiment, first rear compressed portions 15F, 15F are extended rearwardly from the first compressed portions 11F, 11F in such a manner that they gradually approach each other toward the rear end edge 1d and are connected to each other inside the rear end edge 1d through a connecting compressed portion 17F in the shape of a curved line.

Outside the first rear compressed portions 15F, 15F, moreover, second rear compressed portions 18F, 18F are provided and connected to each other inside the rear end edge 1d through a connecting compressed portion 19F in the shape of a curved line. The second rear compressed portions 18F, 18F are also provided with portions that gradually approach each other toward the rear end edge 1d. The first rear compressed portions 15F function as first rear flexible hinges, while the second rear compressed portions 18F function as second rear flexible hinges.

In this embodiment, the region surrounded by the first compressed portions 11F, 11F and the lateral compressed portion 13F is the central absorbent portion 5F, while the region surrounded by the first rear compressed portions 15F, 15F and the connecting compressed portion 17F is the rear central absorbent portion 5G. The bulky central absorbent layer 4A continuously extends over the central absorbent portion 5F and the rear central absorbent portion 5G, between the topsheet 3 and the backsheet 2. In the central absorbent portion 5F and the rear central absorbent portion 5G, the density and basis weight of the central absorbent layer 4A are almost uniform.

Between the first rear compressed portions 15F, 15F and the second rear compressed portions 18F, 18F, moreover, there are provided rear support portions 6F, 6F. The rear support portions 6F, 6F have rear support absorbent layers, between the topsheet 3 and the backsheet 2, which have a higher density than the central absorbent layer 4A in the rear central absorbent portion 5G. The density of the rear support absorbent layers is equal to or slightly lower than that in the support portions 6, 6 and higher than that of the central absorbent layer 4A.

Furthermore, the relationship between the thickness of the central absorbent layer 4A in the rear central absorbent portion 5G and the first rear compressed portions 15F and the second rear compressed portions 18F is almost similar to the relationship between H and h shown in the section of FIG. 2, so that the first rear compressed portions 15F and the second rear compressed portions 18F are positioned sufficiently lower than the midpoint of the thickness of the rear central absorbent portion 5G.

As shown in FIG. 13, boundary portions 11G, 11G between the first rear compressed portions 15F, 15F and the first compressed portions 11F, 11F are curved away from the longitudinal centerline Oy—Oy, so that the central absorbent layer 4A is widened at these boundary portions 11G, 11G. The first rear compressed portions 15F, 15F gradually approach each other as they extend from the boundary portions 11G, 11G toward the rear end edge 1d, while the first compressed portions 11F, 11F also gradually approach each other as they extend from the boundary portions 11G, 11G to the lateral reference line Ox—Ox.

That is, the central absorbent layer 4A is gradually narrowed as it extends forward and rearward from the boundary portions 11G, 11G.

It should be noted that front ends 18G, 18G of the second rear compressed portions 18F, 18F are located closer to the rear end edge 1d than the boundary portions 11G, 11G, wherein the front ends 18G, 18G face the first rear compressed portions 15F, 15F at a predetermined spacing. In this preferred embodiment, an imaginary extension fx, which is extended forwardly from the center of the front end 18G of the second rear compressed portion 18F in parallel with the longitudinal centerline Oy—Oy, intersects the first rear compressed portion 15F.

In the sanitary napkin 1F of FIG. 13, moreover, the liquid-impermeable sheets 20, 20 are laid on both sides, so that the leakage preventing walls 21, 21 are formed of the liquid-impermeable sheets 20, 20. As has been described hereinabove, the leakage prevented walls 21, 21 are provided with the elastic members 22 for producing a longitudinal elastic shrinkage force. The elastic members 22 exert the longitudinal elastic shrinkage force on the sanitary napkin 1F.

When the long sanitary napkin 1F is worn as attached to the inner side of the groin piece 25 of the undergarment, the lateral reference line Ox—Ox can match the longitudinal nearly center of the vaginal opening. When the compressive force F is applied to the vicinity of the lateral reference line Ox—Ox from the thighs, therefore, the sanitary napkin 1F at this portion can be deformed in the same manner as shown in FIGS. 4 and 5 by the action of the support portions 6, 6, so that the central absorbent portion 5F can be brought into close contact with the vaginal opening.

On the other hand, the rear portion of the sanitary napkin 1F is brought into contact with the buttocks so that the rear central absorbent portion 5G may fit in the cleft of the buttocks. At this time, the thighs exert a compressive force on the rear central absorbent portion 5G. In addition, the groin piece 25 of the undergarment exerts a tightening force (i.e., a lifting force which presses the sanitary napkin against the wearer's crotch along the longitudinal centerline Oy—Oy) on the sanitary napkin 1F. Accordingly, since the sanitary napkin 1F whose rear portion (hip-guard) is kept in close contact with the wearer's buttocks is pressed against the wearer's crotch at the lateral reference line Ox—Ox and the vicinity thereof due to the lifting force of the groin piece of the undergarment, the rear portion of the sanitary napkin 1F is subjected to a force that tends to shorten the length. In this embodiment, furthermore, the elastic members 22 provided in the leakage preventing walls 21, 21 also exert an elastic force that tends to make the front end edge 1c and the rear end edge 1d approach each other.

Due to the individual forces or combinations thereof, the second rear compressed portions 18F, 18F are subjected to a force that will be transmitted forward along the imaginary extension fx or forces F1, F1 that will be transmitted forward across the first rear compressed portions 15F, 15F, as indicated by arrows in FIG. 13. These forces function to lift up the central absorbent layer 4A that is widened at the boundary portions 11G, 11G toward the wearer's crotch. More specifically, when the forward force or the forces F1, F1 are exerted on the second rear compressed portions 18F, 18F, the front ends 18G, 18G of the second rear compressed portions 18F, 18F get under the first rear compressed portions 15F, 15F, so that the rear support portions 6F, 6F are deformed and the central absorbent layer 4A that is widened at the boundary portions 11G, 11G is lifted up toward the wearer's crotch.

As a result, the widened portion of the central absorbent layer 4A can easily contact the perineum (i.e., the area between the posterior part of the vaginal opening and the anus). Therefore, menstrual blood discharged from the vaginal opening can be easily blocked at the perineum during both nighttime and daytime, preventing leakage toward the buttocks. Since the central absorbent layer 4A that is in close contact with the perineum is supported from below by the front ends 18G, 18G and the rear support portions 6F, 6F, the central absorbent layer 4A is hardly crushed even when a body pressure is exerted thereon, so that it can be easily kept in close contact with the perineum at all times.

Figure 14:
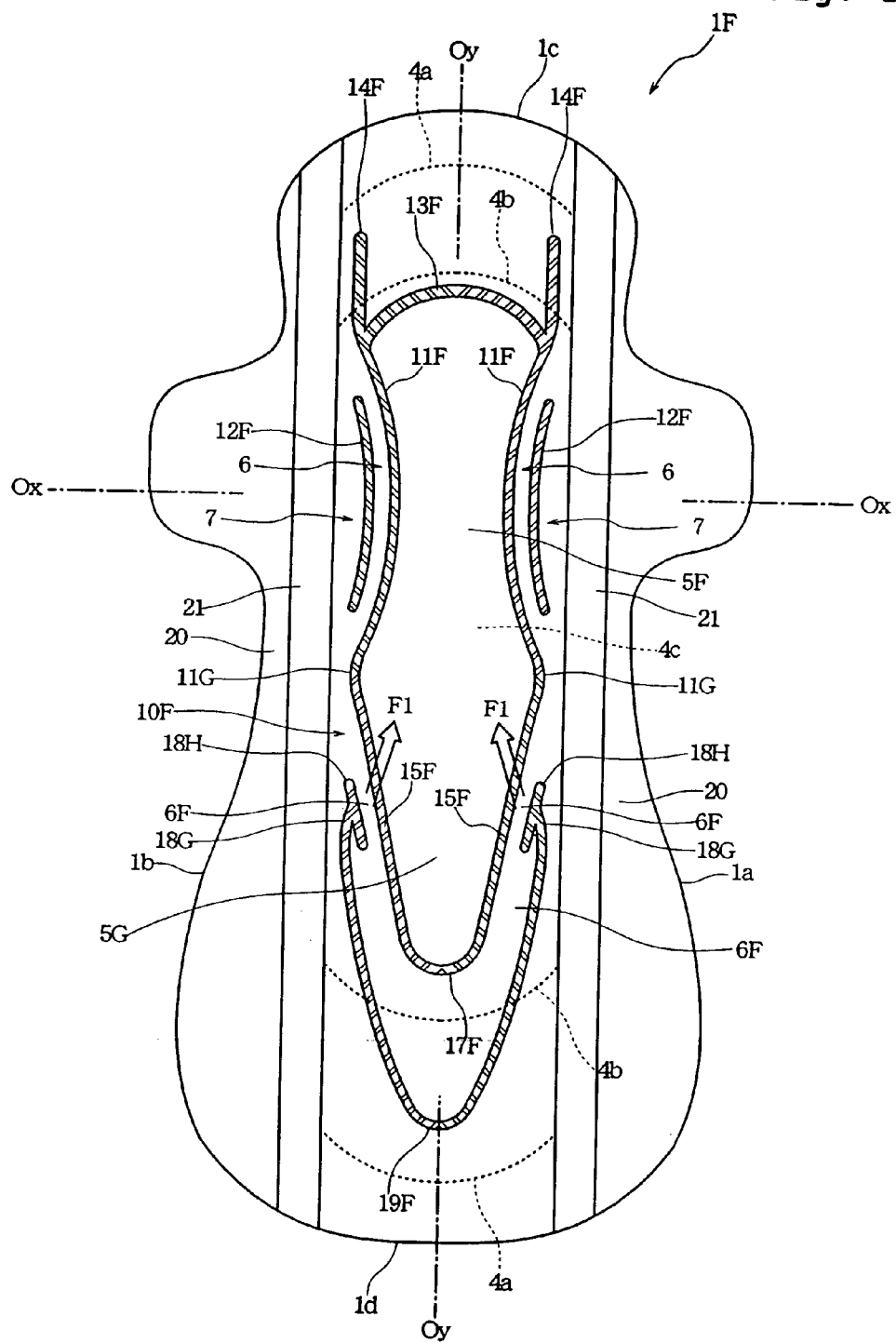
FIG. 14 is a top plan view showing a sanitary napkin according to an eighth embodiment of the present invention.

FIG. 14 shows a modification of the sanitary napkin 1F.

In the sanitary napkin 1F of FIG. 14, whose structure is substantially the same as that of FIG. 13, additional compressed portions 18H, 18H in the shape of a short line are formed at the front ends 18G, 18G of the second rear compressed portions 18F, 18F. The compressed portions 18H, 18H are placed side by side with the first rear compressed portions 15F, 15F, so that the rear support portions 6F, 6F, in which the absorbent layer is maintained in a highly compressed state, are formed between the compressed portions 18H, 18H and the first rear compressed portions 15F, 15F.

In this modification, when the second rear compressed portions 18F, 18F are subjected to the forward force or the forces F1, F1 that will be transmitted across the first rear compressed portions 15F, 15F, these forces act on the first rear compressed portions 15F, 15F over a wide area, through the compressed portions 18H, 18H and the rear support portions 6F, 6F. As a result, since the rear support portions 6F, 6F can be deformed to have the compressed portions 18H, 18H under the first rear compressed portions 15F, 15F, the central absorbent layer 4A can be lifted up toward the wearer's crotch over a wide area in the vicinity of the boundary portions 11G, 11G.

Figure 15:
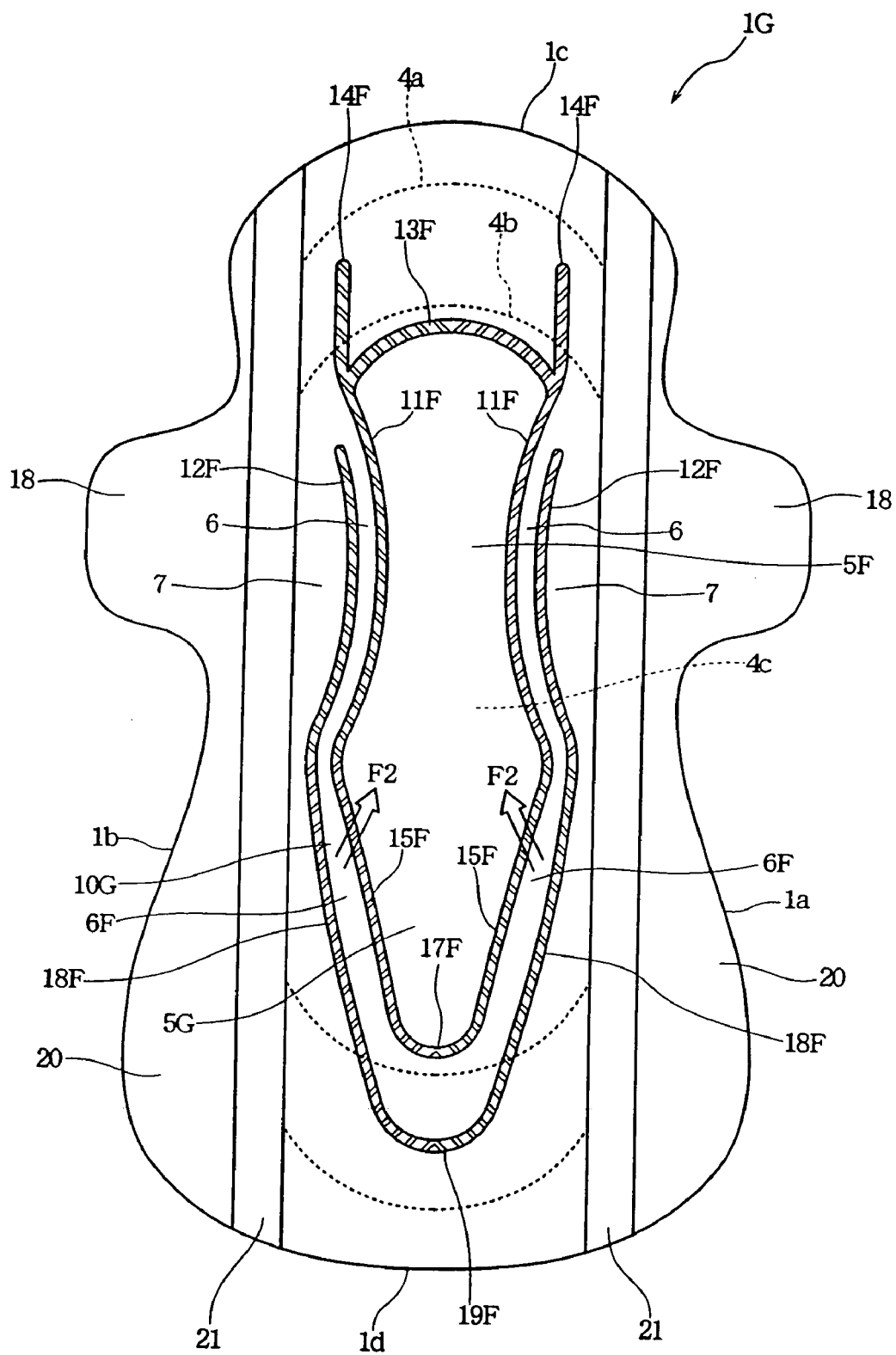
FIG. 15 is a top plan view showing a sanitary napkin as a modification of the eighth embodiment of the present invention.

FIG. 15 is a top plan view showing a sanitary napkin 1G according to an eighth embodiment of the present invention.

Although a hip-guard is provided at its rear portion, the sanitary napkin 1G of FIG. 15 is of a slightly shorter longitudinal dimension than the sanitary napkin 1F of FIG. 13.

The sanitary napkin 1G has compressed portions 10G that are formed in the substantially same pattern as the compressed potions 10F of FIG. 13, except that the second compressed portions 12F, 12F are continued to the second rear compressed portions 18F, 18F.

In the sanitary napkin 1G, the first rear compressed portions 15F, 15F and the second rear compressed portions 18F, 18F are arranged in a side-by-side relationship, without intersecting each other, so that the rear support portions 6F, 6F whose absorbent layer has a higher density than the central absorbent layer 4A are formed between the first rear compressed portions 15F, 15F and the second rear compressed portions 18F, 18F.

When the sanitary napkin 1G is worn in the wearer's crotch, the central absorbent portion 5F between the first compressed portions 11F and 11F is lifted up toward the vaginal opening. At this time, if a force that tends to shorten the longitudinal dimension is exerted, as set forth above, a forward force or forces F2, F2 that will be transmitted across the first rear compressed portions 15F, 15F act on the second rear compressed portions 18F, 18F and the rear support portions 6F, 6F. Due to these forces, the rear support portions 6F, 6F are deformed in the substantially same manner as the support portions 6, 6 shown in FIG. 4, so that the rear central absorbent portion 5G is lifted up toward the wearer's crotch, coming into close contact with the perineum at a portion near the boundary portions 11G, 11G.

In case where the sanitary napkin 1F is worn together with a sanitary panty in which an elastic member is provided from a groin piece to a back body to extend along the cleft of the wearer's buttocks, the rear central absorbent portion 5G is pushed into the cleft of the buttocks due to a force of the elastic member. Also at this time, since the first rear compressed portions 15F, 15F and the second rear compressed portions 18F, 18F can serve as the flexible hinges on both sides of the rear support portions 6F, 6F, the rear support portions 6F, 6F can be easily bent, so that even when subjected to the pushing force from the undergarment, the rear central absorbent portion 5G can be easily brought into close contact with the perineum.

Figure 16:
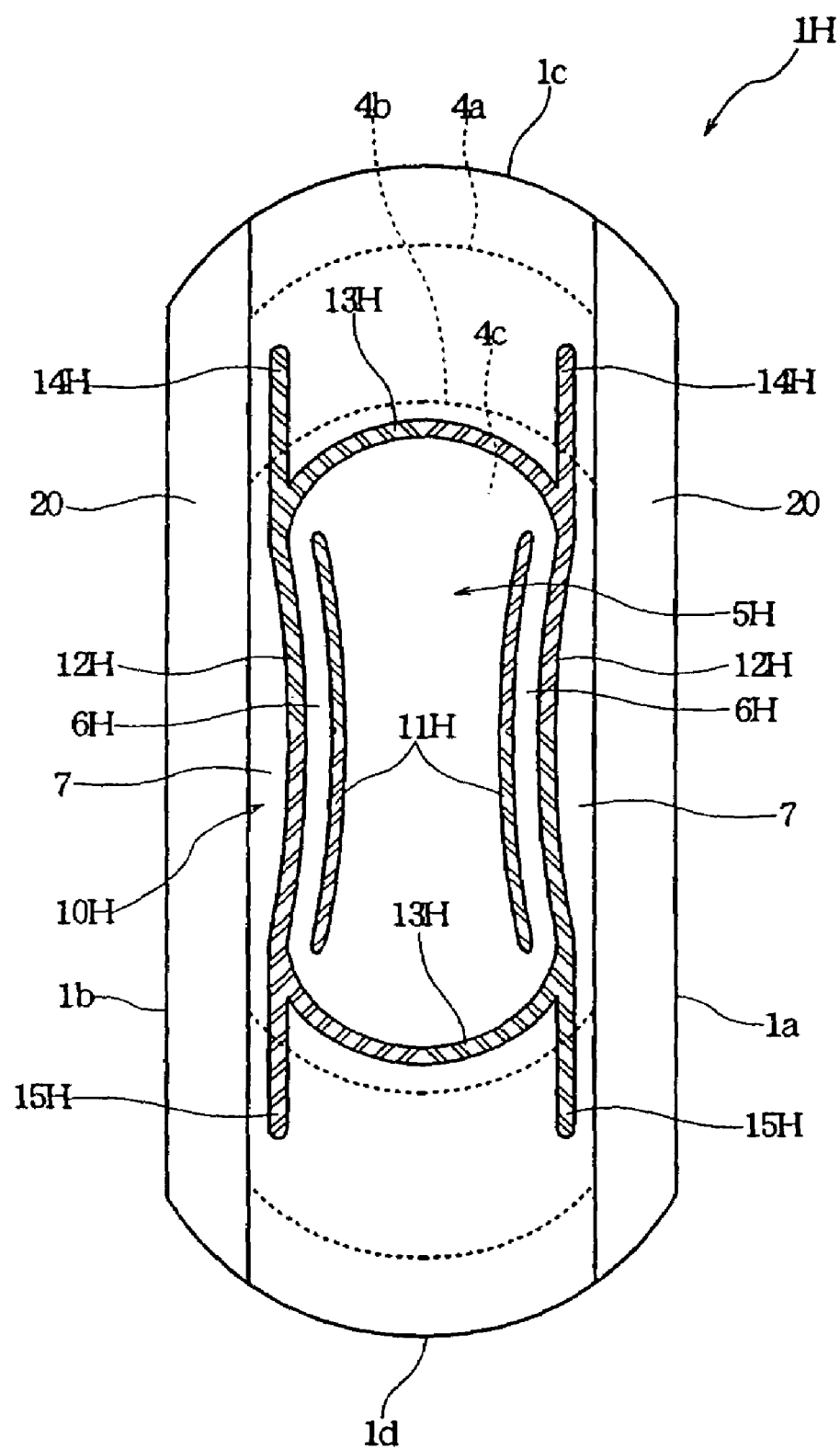
FIG. 16 is a top plan view showing a sanitary napkin according to a ninth embodiment of the present invention.

FIG. 16 is a top plan view showing a sanitary napkin 1H according to a ninth embodiment of the present invention.

The structure of the sanitary napkin 1H is similar to that of the sanitary napkin 1 shown in FIG. 1, except that the wings 18 are eliminated.

The sanitary napkin 1H of FIG. 16 has compressed portions 10H comprising first compressed portion 11H, 11H that extend in the shape of an arcuate line and second compressed portions 12H, 12H that also extend in the shape of an arcuate line outside the former, wherein the first compressed portion 11H, 11H are spaced a constant distance apart from the second compressed portions 12H, 12H. The region between the first compressed portion 11H, 11H is a central absorbent portion 5H, while the regions between the first compressed portion 11H, 11H and the second compressed portions 12H, 12H are support portions 6H, 6H.

The second compressed portions 12H, 12H are connected to each other through lateral compressed portions 13H, 13H provided at front and rear portions. Therefore, the first compressed portion 11H, 11H and the support portions 6H, 6H are located inside the region surrounded by the second compressed portions 12H, 12H and the lateral compressed portions 13H, 13H.

Furthermore, forwardly extending compressed portions 14H, 14H and rearwardly extending compressed portions 15H, 15H are formed to extend continuously from the second compressed portions 12H, 12H.

When the sanitary napkin 1H is worn, the support portions 6H, 6H are deformed to bring the central absorbent portion 5H into close contact with the vaginal opening, as shown in FIGS. 4 and 5.

In this embodiment, since the region surrounded by the second compressed portions 12H, 12H and the lateral compressed portions 13H, 13H has a larger area than the central absorbent portion 5H, liquid absorption capacity of the surrounded region can be made large. In addition, since diffusion of menstrual blood applied to the support portions 6H, 6H between the first compressed portion 11H, 11H and the second compressed portions 12H, 12H can be limited in the surrounded region, leakage of menstrual blood from the sanitary napkin 1H can be prevented easily.

Figure 17:
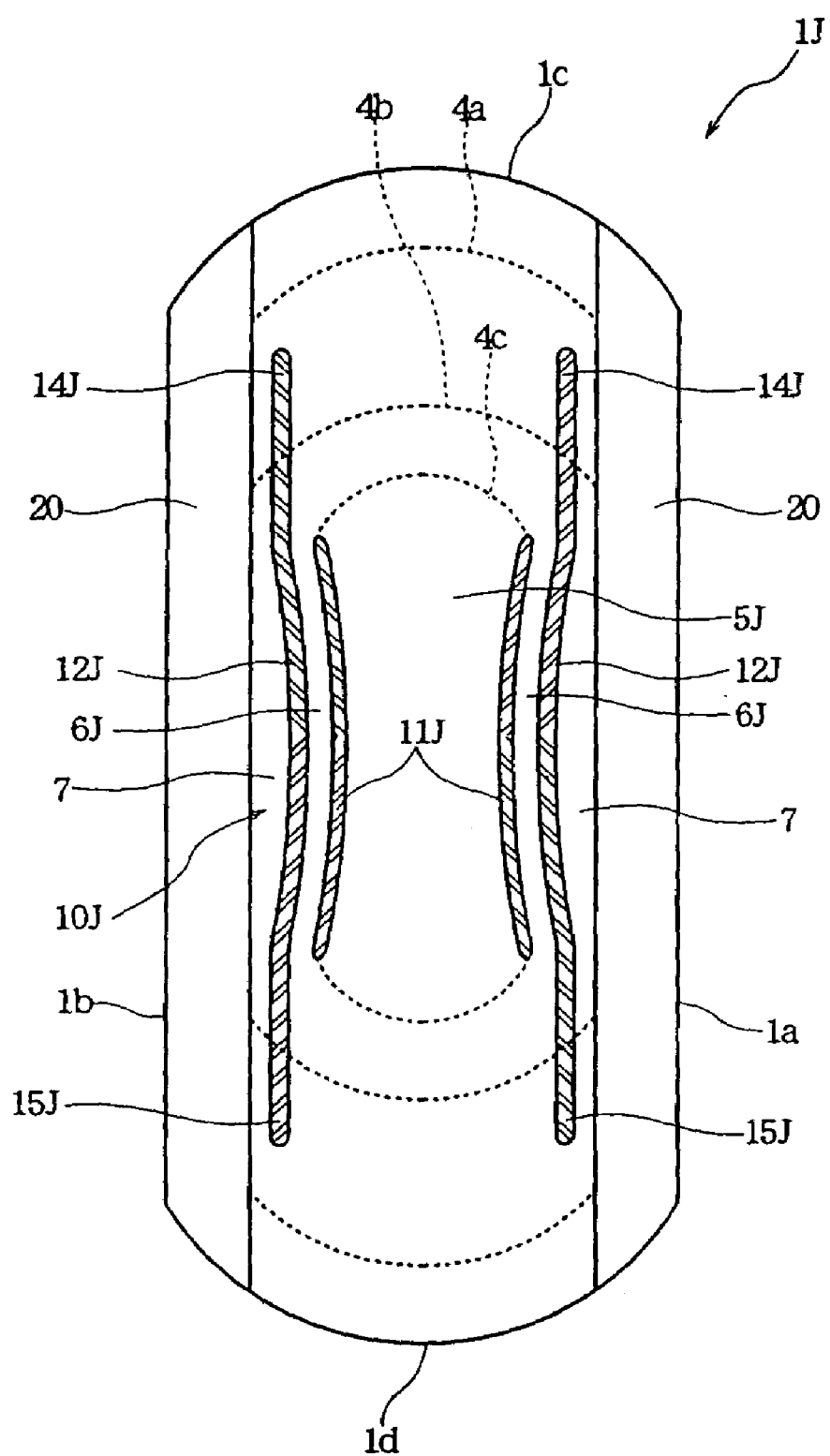
FIG. 17 is a top plan view showing a sanitary napkin according to a tenth embodiment of the present invention.

FIG. 17 is a top plan view showing a sanitary napkin 1J according to a tenth embodiment of the present invention.

The sanitary napkin 1J has compressed portions 10J whose pattern is slightly changed from that in the sanitary napkin 1E of FIG. 12. In this embodiment, forwardly extending compressed portions 14J, 14J and rearwardly extending compressed portions 15J, 15J are continuously extended forwardly and rearwardly from second compressed portions 12J, 12J. On the other hand, first compressed portions 11J, 11J are provided in the region between the second compressed portions 12J, 12J. The region between the first compressed portions 11J, 11J is a central absorbent portion 5J.

Also in this embodiment, the central absorbent portion 5J can be lifted up toward the wearer's body and brought into close contact with the vaginal opening by the action of support portions 6J, 6J. In addition, since region outside the central absorbent portion 5J is positioned between the second compressed portions 12J, 12J, the forwardly extending compressed portions 14J, 14J and the rearwardly extending compressed portions 15J, 15J over a long range in the longitudinal direction, menstrual blood adhered to the support portions 6J, 6J can be diffused in the longitudinal direction of the sanitary napkin 1J, thereby improving the effect of preventing lateral leakage.

According to the present invention, as has been described hereinabove, when the absorbent article as worn in the wearer's crotch is subjected to a lateral compressive force, the central absorbent portion can easily come into close contact with the wearer's excretory part. In addition, even after absorption of discharged liquid, the central absorbent portion can be certainly kept in close contact with the wearer's excretory part. Therefore, leakage of the discharged liquid can be easily prevented.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the feature set out in the appended claims.

What is claimed is:

1. An absorbent article comprising:
a liquid-permeable topsheet on a skin surface; and
a backsheet on a garment surface,
wherein first flexible hinges and second flexible hinges are formed to extend longitudinally of the absorbent article, the first flexible hinges being disposed symmetrically about a longitudinal centerline of the absorbent article to define a central absorbent portion, the second flexible hinges being disposed symmetrically about the longitudinal centerline and spaced outwardly apart from the first flexible hinges to define support portions between adjacent first and second flexible hinges and side portions outside the second flexible hinges, the first flexible hinges facilitating bending of the support portions from the central absorbent portion, and the second flexible hinges facilitating bending of the side portions from the support portions,
wherein an absorbent layer is disposed between the topsheet and the backsheet in both the central absorbent portion and the support portions, the absorbent layer having a higher basis weight in the central absorbent portion than in the support portions, so that when no external force is exerted on the absorbent article, the support portions, as well as the first and second flexible hinges, are located below a midpoint of thickness of the central absorbent portion.

2. An absorbent article as set forth in claim 1, wherein when a compressive force toward the longitudinal centerline is exerted on the individual second flexible hinges, the individual support portions are displaced to have the first flexible hinge higher than the second flexible hinge, thereby lifting up the central absorbent portion.

3. An absorbent article as set forth in claim 1, wherein the individual support portions have a reinforcing member whose density is higher than that of the absorbent layer in the central absorbent portion.

4. An absorbent article as set forth in claim 1, wherein when a compressive force toward the longitudinal centerline is exerted on the individual second flexible hinges, the central absorbent portion and the support portions are deformed so that the individual first flexible hinges get under the absorbent layer provided in the central absorbent portion.

5. An absorbent article as set forth in claim 1, wherein the support portions approach each other the nearest at a lateral reference line of the absorbent article, and gradually go away from the longitudinal centerline as they extend away from the lateral reference line toward longitudinally opposed ends of the absorbent article.

6. An absorbent article as set forth in claim 1, wherein the individual support portions are in the shape of a line curved toward the centerline.

7. An absorbent article as set forth in claim 1, wherein the individual support portions have a portion of constant width, over which the first and second flexible hinges are spaced a constant distance apart from each other.

8. An absorbent article as set forth in claim 1, wherein the absorbent layer extends over the central absorbent portion, across the support portions, to the side portions.

9. An absorbent article as set forth in claim 8, wherein the first and second flexible hinges are formed by compressing the absorbent layer.

10. An absorbent article as set forth in claim 8, wherein the individual support portions have a width of 5 to 15 mm, in which the absorbent layer is compressed, so that a boundary line between the support portion and the central absorbent portion functions as the first flexible hinge while a boundary line between the support portion and the side portion functions as the second flexible hinge.

11. An absorbent article as set forth in claim 1, wherein the absorbent layer is absent in the first and second flexible hinges.

12. An absorbent article as set forth in claim 1, wherein the central absorbent portion is surrounded by the first flexible hinges and longitudinally opposed lateral flexible hinges connecting the first flexible hinges, and the second flexible hinges are located outside the central absorbent portion.

13. An absorbent article as set forth in claim 1, wherein the first flexible hinges are located inside a region surrounded by the second flexible hinges and longitudinally opposed lateral flexible hinges connecting the second flexible hinges.

14. An absorbent article as set forth in claim 1, wherein first rear flexible hinges are extended rearwardly continuously from the first flexible hinges to gradually approach each other, and second rear flexible hinges are extended rearwardly to gradually approach each other while being spaced outwardly apart from the first rear flexible hinges, to thereby define rear support portions between adjacent first and second rear flexible hinges.

15. An absorbent article as set forth in claim 14, wherein the second rear flexible hinges are extended continuously from the second flexible hinges.

16. An absorbent article as set forth in claim 14, wherein the first and second rear flexible hinges are formed by compressing the absorbent layer.

17. An absorbent article as set forth in claim 16, wherein a rear central absorbent portion is defined between the first rear flexible hinges, and the rear support portions have an absorbent layer that is of a higher density than that provided in the rear central absorbent portion.

18. An absorbent article as set forth in claim 1, which is a sanitary napkin.

19. An absorbent article as set forth in claim 1, wherein when no external force is exerted on the absorbent article, h is smaller than H/6, wherein H indicates a thickness of the central absorbent portion at the longitudinal centerline while h indicates a height measured from an exterior surface of the backsheet to a midpoint of thickness of the first and second flexible hinges.

20. An absorbent article comprising:
a liquid-permeable topsheet on a skin surface; and
a backsheet on a garment surface,
wherein first rear compressed portions are disposed symmetrically about a longitudinal centerline of the absorbent article to define a rear central absorbent portion having an absorbent layer therebetween, the first rear compressed portions extending rearwardly of the absorbent article to gradually approach each other, and second rear compressed portions are disposed symmetrically about the longitudinal centerline, the second rear compressed portions extending rearwardly of the absorbent article while being spaced outwardly apart from the first rear compressed portions,
wherein front ends of the second rear compressed portions are spaced a predetermined distance behind a line on which a lateral distance between the first rear compressed portions is increased to a maximum.

21. An absorbent article as set forth in claim 20, wherein portions defined between adjacent first and second rear compressed portions have an absorbent layer that is of a higher density than that provided in the rear central absorbent portion.

22. An absorbent article as set forth in claim 20, wherein an imaginary extension, which is extended forwardly from the front end of the second rear compressed portion in parallel with the longitudinal centerline, intersects the first rear compressed portion.

23. An absorbent article as set forth in claim 20, wherein additional compressed portions are formed at the front ends of the second rear compressed portions and placed side by side with the first rear compressed portions.

24. An absorbent article as set forth in claim 20, wherein first compressed portions are extended forwardly from the first rear compressed portions to gradually approach each other until a lateral reference line of the absorbent article.

25. An absorbent article as set forth in claim 20, wherein a longitudinal shrinkage force is exerted on the absorbent article, at least at locations where the front ends of the second rear compressed portions face the first rear compressed portions.

* * * * *